United States Patent
Payne et al.

(10) Patent No.: US 10,399,937 B2
(45) Date of Patent: Sep. 3, 2019

(54) IONIZABLE CATIONIC LIPID FOR RNA DELIVERY

(71) Applicant: Arcturus Therapeutics, Inc., San Diego, CA (US)

(72) Inventors: Joseph E. Payne, San Diego, CA (US); Padmanabh Chivukula, San Diego, CA (US)

(73) Assignee: Arcturus Therapeutics, Inc., San Diego, CA (US)

(*) Notice: Subject to any disclaimer, the term of this patent is extended or adjusted under 35 U.S.C. 154(b) by 0 days.

(21) Appl. No.: 15/899,314

(22) Filed: Feb. 19, 2018

(65) Prior Publication Data

US 2018/0170865 A1    Jun. 21, 2018

Related U.S. Application Data

(60) Continuation of application No. 15/614,499, filed on Jun. 5, 2017, now Pat. No. 9,896,413, which is a continuation of application No. 15/347,647, filed on Nov. 9, 2016, now Pat. No. 9,670,152, which is a division of application No. 14/707,796, filed on May 8, 2015, now Pat. No. 9,567,296, which is a continuation-in-part of application No. 14/546,105, filed on Nov. 18, 2014, now Pat. No. 9,593,077.

(60) Provisional application No. 61/905,724, filed on Nov. 18, 2013.

(51) Int. Cl.
| | |
|---|---|
| C07C 323/52 | (2006.01) |
| C07C 271/22 | (2006.01) |
| C07C 333/04 | (2006.01) |
| C07C 235/12 | (2006.01) |
| C07C 237/12 | (2006.01) |
| C07C 323/25 | (2006.01) |
| C07C 323/60 | (2006.01) |
| A61K 47/18 | (2017.01) |
| A61K 47/20 | (2006.01) |
| C07J 41/00 | (2006.01) |
| C12N 15/113 | (2010.01) |
| C12N 15/11 | (2006.01) |
| C11C 3/04 | (2006.01) |

(52) U.S. Cl.
CPC ............ *C07C 323/52* (2013.01); *A61K 47/18* (2013.01); *A61K 47/20* (2013.01); *C07C 235/12* (2013.01); *C07C 237/12* (2013.01); *C07C 271/22* (2013.01); *C07C 323/25* (2013.01); *C07C 323/60* (2013.01); *C07C 333/04* (2013.01); *C07J 41/0055* (2013.01); *C11C 3/04* (2013.01); *C12N 15/111* (2013.01); *C12N 15/113* (2013.01); *C12N 15/1137* (2013.01); *C12N 2310/14* (2013.01); *C12N 2320/32* (2013.01)

(58) Field of Classification Search
CPC ... C07C 271/22; C07C 333/04; C07C 323/25; A61K 47/18; A61K 47/20
See application file for complete search history.

(56) References Cited

U.S. PATENT DOCUMENTS

| | | | |
|---|---|---|---|
| 4,511,069 A | 4/1985 | Kalat | |
| 4,778,810 A | 10/1988 | Wenig et al. | |
| 5,849,902 A | 12/1998 | Aarow et al. | |
| 9,011,903 B2 | 4/2015 | Niitsu et al. | |
| 9,365,610 B2 | 6/2016 | Payne et al. | |
| 9,567,296 B2 | 2/2017 | Payne et al. | |
| 9,580,711 B2 | 2/2017 | Payne et al. | |
| 9,593,077 B2 | 3/2017 | Payne et al. | |
| 9,670,152 B2 | 6/2017 | Payne et al. | |
| 9,850,202 B2 | 12/2017 | Payne et al. | |
| 9,896,413 B2 * | 2/2018 | Payne | C07C 323/25 |
| 9,951,002 B2 | 4/2018 | Payne et al. | |
| 2012/0027803 A1 | 2/2012 | Manoharan et al. | |

(Continued)

FOREIGN PATENT DOCUMENTS

| | | |
|---|---|---|
| CN | 102884041 A | 1/2013 |
| EP | 1502576 A2 | 2/2005 |

(Continued)

OTHER PUBLICATIONS

U.S. Appl. No. 14/707,876, filed May 8, 2015, Payne et al.

(Continued)

*Primary Examiner* — Paul A Zucker
(74) *Attorney, Agent, or Firm* — Baker Hostetler

(57) ABSTRACT

What is described herein are cationic lipids that facilitate the intracellular delivery of biologically active molecules, comprising a compound of formula I

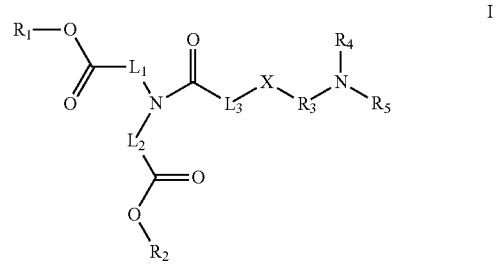

wherein $R_1$ is a linear alkyl, alkenyl, or alkynyl of 2 to 12 carbons, or a branched alkyl with 7-25 $R_2$ is a branched alkenyl with 7-25 carbons, $L_1$ and $L_2$ are independently a linear alkenylene with 2-18 carbons, X is S or O, $L_3$ is a bond, and $R_3$ $R_4$, and $R_5$ are each a linear or branched alkylene with 1-6 carbons.

14 Claims, 4 Drawing Sheets

(56) References Cited

U.S. PATENT DOCUMENTS

| | | |
|---|---|---|
| 2013/0022665 A1 | 1/2013 | Niitsu et al. |
| 2013/0129811 A1 | 5/2013 | Kuboyama et al. |
| 2013/0274504 A1 | 10/2013 | Colletti et al. |
| 2013/0280305 A1 | 10/2013 | Kuboyama et al. |
| 2015/0141678 A1 | 5/2015 | Payne et al. |
| 2017/0114010 A1 | 4/2017 | Payne et al. |
| 2018/0169268 A1 | 6/2018 | Payne et al. |
| 2018/0170866 A1 | 6/2018 | Payne et al. |
| 2018/0208555 A1 | 7/2018 | Payne et al. |

FOREIGN PATENT DOCUMENTS

| | | | |
|---|---|---|---|
| FR | 1481016 A | 5/1967 | |
| JP | 61-089286 | 5/1986 | |
| JP | 61-136584 | 6/1986 | |
| WO | WO 1992/007065 A1 | 4/1992 | |
| WO | WO 1993/015187 A1 | 8/1993 | |
| WO | WO 2012/170952 A2 | 12/2002 | |
| WO | WO 2012/170952 A3 | 12/2002 | |
| WO | WO 2012/170952 A9 | 12/2002 | |
| WO | WO 2010/061880 A1 | 6/2010 | |
| WO | WO 2011/136368 A1 | 11/2011 | |
| WO | WO 2011/153493 A2 | 12/2011 | |
| WO | WO 2013/065825 A1 | 5/2013 | |
| WO | WO 2013/086373 A1 | 6/2013 | |
| WO | WO 2013/185116 A1 | 12/2013 | |
| WO | WO-2013185116 A1 * | 12/2013 | ............. A61K 47/18 |
| WO | WO 2013/065825 A1 | 4/2015 | |
| WO | WO 2015/074085 A1 | 5/2015 | |
| WO | WO 2016/081029 A1 | 5/2016 | |

OTHER PUBLICATIONS

International Patent Application No. PCT/US2014/066242; Int'l Search Report and the Written Opinion; dated Feb. 10, 2015; 10 pages.

International Patent Application No. PCT/US2015/030218; Int'l Search Report and the Written Opinion; dated Aug. 25, 2015; 10 pages.

Dorwald; "Side Reactions in Organic Synthesis—A Guide to Successful Synthesis Design"; Wiley-VCH; Preface; .Copyrgt. 2005; 4 pages.

"Virtual Textbook of Organic Chemistry"; https://www2.chemistry.msu.edu/faculty/reusch/virttxtjml/intro1.htm; William Reusch; .Copyrgt. 1999; accessed Jul. 13, 2016; 4 pages.

"Heterecyclic Chemistry—Heterocyclic Compounds"; http://www2.chemistry.msu.edu/faculty/reusch/virttxtjml/heterocy.htm; William Reusch; .Copyrgt. 1999; accessed Jul. 13, 2016; 14 pages.

Zaragoza Dorwald, Side Reactions in Organic Synthesis, 2005, Wiley-VCH Verlag GmbH & Co. KGaA, Weinheim, Preface. p. IX.

International Patent Application No. PCT/US2015/030218; Int'l Preliminary Report on Patentability; dated Jun. 1, 2017; 8 pages.

International Patent Application No. PCT/US2017/015886; Int'l Search Report and the Written Opinion; dated Aug. 29, 2017; 12 pages.

International Patent Application No. PCT/US2017/067756; Int'l Search Report and the Written Opinion; dated Mar. 26, 2018; 11 pages International Patent Application No. PCT/US2017/015886; Int'l Preliminary Report on Patentability; dated May 23, 2019; 48 pages.

* cited by examiner

IONIZABLE CATIONIC LIPID FOR RNA DELIVERY

CROSS REFERENCE TO RELATED APPLICATIONS

This application is a continuation of U.S. patent application Ser. No. 15/614,499, filed Jun. 5, 2017, now U.S. Pat. No. 9,896,413, issued Feb. 20, 2018, which is a continuation of U.S. patent application Ser. No. 15/347,647, filed Nov. 9, 2016, now U.S. Pat. No. 9,670,152, granted Jun. 6, 2017, which is a divisional of U.S. patent application Ser. No. 14/707,796, filed May 8, 2015, now U.S. Pat. No. 9,567,296, issued Feb. 14, 2017, which is a continuation-in-part and claims benefit under 35 U.S.C. § 120 to U.S. patent application Ser. No. 14/546,105 filed on Nov. 18, 2014, now U.S. Pat. No. 9,593,077, issued Mar. 14, 2017, which claims benefit under 35 U.S.C. § 119(e) of Provisional U.S. Patent Application No. 61/905,724, filed Nov. 18, 2013, the contents of which are incorporated herein by reference in its entirety.

The description of U.S. patent application Ser. No. 14/707,876, entitled "IONIZABLE CATIONIC LIPID FOR RNA DELIVERY," filed May 8, 2015, now U.S. Pat. No. 9,365,610, issued Jun. 14, 2016, is hereby incorporated by reference in its entirety.

BACKGROUND

A number of different types of nucleic acids are currently being developed as therapeutics for the treatment of a number of diseases. These nucleic acids include DNA in gene therapy, plasmids-based interfering nucleic acids, small interfering nucleic acids for use in RNA interference (RNAi), including siRNA, miRNA, antisense molecules, ribozymes and aptamers. As these molecules are being developed, there has been developed a need to produce them in a form that is stable and has a long shelf-life and that can be easily incorporated into an anhydrous organic or anhydrous polar aprotic solvent to enable encapsulations of the nucleic acids without the side-reactions that can occur in a polar aqueous solution or nonpolar solvents.

The present invention relates to novel lipid compositions that facilitate the intracellular delivery of biologically active and therapeutic molecules. The present invention relates also to pharmaceutical compositions that comprise such lipid compositions, and that are useful to deliver therapeutically effective amounts of biologically active molecules into the cells of patients.

The delivery of a therapeutic compound to a subject is important for its therapeutic effects and usually it can be impeded by limited ability of the compound to reach targeted cells and tissues. Improvement of such compounds to enter the targeted cells of tissues by a variety of means of delivery is crucial. The present invention relates the novel lipids, in compositions and methods for preparation that facilitate the targeted intracellular delivery of biological active molecules.

Examples of biologically active molecules for which effective targeting to a patient's tissues is often not achieved include: (1) numerous proteins including immunoglobin proteins, (2) polynucleotides such as genomic DNA, cDNA, or mRNA (3) antisense polynucleotides; and (4) many low molecular weight compounds, whether synthetic or naturally occurring, such as the peptide hormones and antibiotics.

One of the fundamental challenges now facing medical practitioners is that a number of different types of nucleic acids are currently being developed as therapeutics for the treatment of a number of diseases. These nucleic acids include DNA in gene therapy, plasmids, small interfering nucleic acids (siNA), siRNA, and microRNA (miRNA) for use in RNA interference (RNAi), antisense molecules, ribozymes, antagomirs, and aptamers. As these nucleic acids are being developed, there is a need to produce lipid formulations that are easy to make and can be readily delivered to a target tissue.

SUMMARY

What is described is a compound of formula I

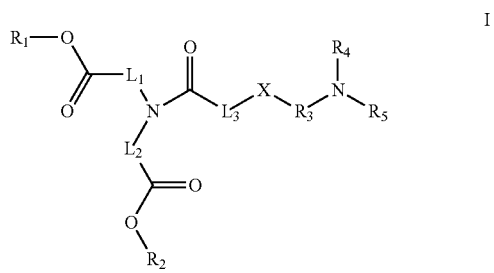

wherein
$R_1$ is a linear alkyl, alkenyl, or alkynyl of 2 to 12 carbons, or a branched alkyl with 25, 24, 23, 22, 21, 20, 19, 18, 17, 16, 15, 14, 13, 12, 11, 10, 9, 8, or 7 carbons,
$R_2$ is a branched alkyl with 25, 24, 23, 22, 21, 20, 19, 18, 17, 16, 15, 14, 13, 12, 11, 10, 9, 8, or 7 carbons,
$L_1$ and $L_2$ are independently a linear alkylene with 1-18 carbons or alkenylene with 2-18 carbons,
X is S or O,
$L_3$ is a bond or an alkylene with 1 to 6 carbons,
$R_3$ is an alkylene with 1 to 6 carbons, and
$R_4$ and $R_5$ are the same or different, each a linear or branched alkyl with 1 to 6 carbons;
or a pharmaceutically acceptable salt thereof.

What is also described herein is a compound of Formula II

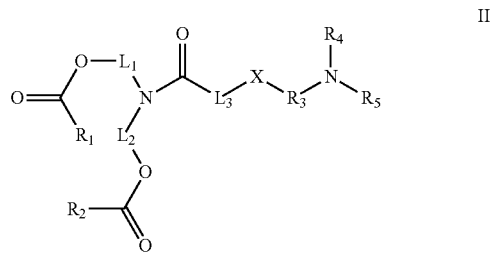

in which
$R_1$ and $R_2$ both consist of a linear alkyl consisting of 1 to 12 carbons, an alkenyl or alkynyl consisting of 2 to 12 carbons,
$L_1$ and $L_2$ both consist of a linear alkylene or alkenylene consisting of 5 to 18 carbons, or forming a heterocycle with N,
X is S,
$L_3$ is a bond or a linear alkylene consisting of 1 to 6 carbons, or forming a heterocycle with N, $R_3$ is a linear or branched alkylene consisting of 1 to 6 carbons, and $R_4$ and $R_5$ are the same or different, each a hydrogen or a linear or branched alkyl consisting of 1 to 6 carbons;

or a pharmaceutically acceptable salt thereof.

In one embodiment of the compound of formula II, $L_1$ and $L_2$ both consist of a linear alkylene consisting of five carbons. In another embodiment of the compound of formula I, $R_3$ is ethylene or propylene. In another embodiment of the compound of formula I, $R_4$ and $R_5$ are the same or different, each hydrogen, methyl, or ethyl. In another embodiment of the compound of formula I, $L_3$ is a bond. In another embodiment of the compound of formula I, $R_1$ and $R_2$ both consist of a linear alkenyl consisting of ten carbons.

What is also described herein is a compound of formula III or IV

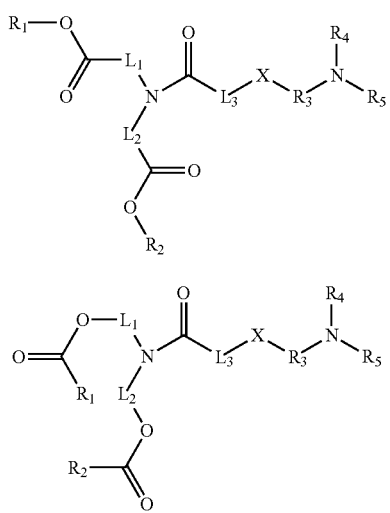

wherein $R_1$ is a branched alkyl with 12 to 20 carbons, $R_2$ is a linear alkyl with 5 to 10 carbons or a branched alkyl with 12 to 20 carbons, $L_1$ and $L_2$ each consist of a bond or a linear alkyl having 1 to 3 carbon atoms, X is S or O, $L_3$ consists of a bond or a lower alkyl, $R_3$ is a lower alkyl, and $R_4$ and $R_5$ are the same or different, each a lower alkyl;

or a pharmaceutically acceptable salt thereof.

In one embodiment of the compound of formula III or IV, $L_3$ is consists of a bond. Another embodiment of the compound of formula III or IV, X is S. In another embodiment of the compound of formula III or IV, $R_3$ is ethylene. In another embodiment of the compound of formula III or IV, $R_3$ is n-propylene or isopropylene. In another embodiment of the compound of formula III or IV, $R_4$ and $R_5$ are separately methyl, ethyl, or isopropyl. In another embodiment of the compound of formula III or IV, $L_1$ and $L_2$ each consist of a bond. In another embodiment of the compound of formula III or IV, $L_1$ and $L_2$ each consist of a methylene. In another embodiment of the compound of formula III or IV, $R_1$ and $R_2$ each consist of branched alkyl. In another embodiment of the compound of formula III or IV, $R_2$ consists of an alkyl. In another embodiment of the compound of formula III or IV, $R_1$ and $R_2$ each consists of 19 or 20 carbon atoms. In another embodiment of the compound of formula III or IV, $R_1$ or $R_2$ each consists of 13 or 14 carbon atoms. In another embodiment of the compound of formula III or IV, $L_3$ consists of methylene, $R_3$ is ethylene, $X_2$ is S, and $R_4$ and $R_5$ are each methyl. In another embodiment of the compound of formula III or IV, wherein $L_3$ consists of a bond, $R_3$ is ethylene, X is S, and $R_4$ and $R_5$ are each methyl. In another embodiment of the compound of formula III or IV, $L_3$ consists of a bond, $R_3$ consists of n-propylene, X consists of S, and $R_4$ and $R_5$ each consist of methyl. In another embodiment of the compound of formula III or IV, $L_3$ consists of a bond, $R_3$ consists of isopropylene, X consists of S, and $R_4$ and $R_5$ each consist of methyl.

The nucleic acid preferably has an activity of suppressing the expression of a target gene. The target gene preferably is a gene associated with inflammation.

What is also described herein is a method for introducing a nucleic acid into a cell of a mammal by using any of the compositions, above. The cell may be in a liver, lung, kidney, brain, blood, spleen, or bone. The composition preferably is administered intravenously, subcutaneously, intraperitoneally, or intrathecally. Preferably, the compositions described herein are used in a method for treating cancer or inflammatory disease. The disease may be one selected from the group consisting of immune disorder, cancer, renal disease, fibrotic disease, genetic abnormality, inflammation, and cardiovascular disorder.

DETAILED DESCRIPTION OF ILLUSTRATIVE EMBODIMENTS

Figure 1:
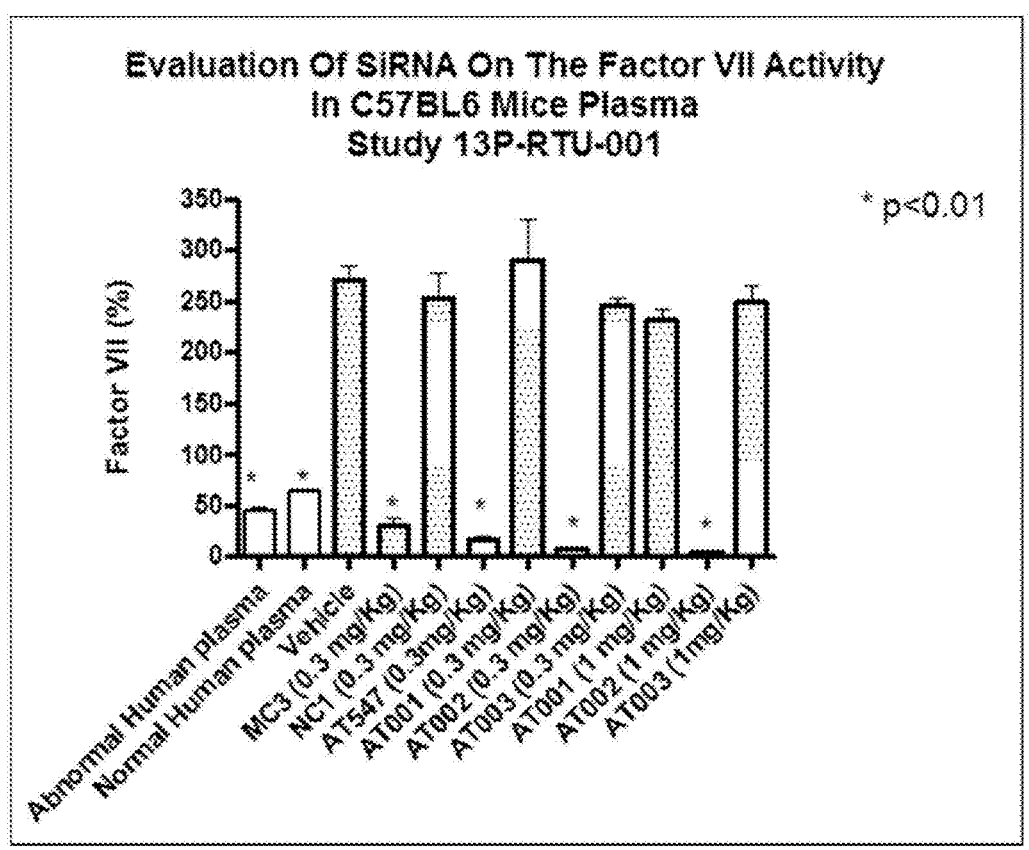
FIG. 1 shows the knockdown activity of siRNA encapsulated by different cationic lipids. The lipids include MC3 (0.3 mg/kg), NC1 (0.3 mg/kg), ATX-547 (0.3 mg/kg), ATX-001 (0.3 and 1.0 mg/kg), ATX-002 (0.3 and 1.0 mg/kg), and ATX-003 (0.3 and 1.0 mg/kg). The amount of Factor VII knockdown in mouse plasma is shown following administration of the siRNA formulation to C57BL6 mice, compared to injection of vehicle alone. The amount of Factor VII in abnormal and normal human plasma is included as a control. Statistically significant decreases in Factor VII levels (p<0.01) is shown by an asterisk (*).

"At least one" means one or more (e.g., 1-3, 1-2, or 1). "Composition" includes a product comprising the specified ingredients in the specified amounts, as well as any product that results, directly or indirectly, from combination of the specified ingredients in the specified amounts.

"In combination with" as used to describe the administration of a compound of formulas 1, I, and II with other medicaments in the methods of treatment of this invention, means-that the compounds of formulas 1, I, and II and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Alkyl" is a saturated or unsaturated, straight or branched, hydrocarbon chain.

In various embodiments, the alkyl group has 1-18 carbons, i.e. is a $C_1$-$C_{18}$ group, or is a $C_1$-$C_{12}$ group, a $C_1$-$C_6$ group, or a $C_1$-$C_4$ group. Independently, in various embodiments, the alkyl group has zero branches (i.e., is a straight chain), one branch, two branches, or more than two branches. "Alkenyl" is an unsaturated alkyl that may have one double bond, two double bonds, or more than two double bonds. "Alkynal" is an unsaturated alkyl that may have one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having one to six carbons in the chain which chain may be straight or branched. Non-limiting examples of suitable alkyl groups include methyl, ethyl, n-propyl, isopropyl, n-butyl, t-butyl, n-pentyl, and hexyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an NH2-alkyl-group, wherein alkyl is as defined above, bound to the parent moiety through the alkyl group.

"Carboxyalkyl" means an HOOC-alkyl-group, wherein alkyl is as defined above, bound to the parent moiety through the alkyl group.

"Commercially available chemicals" and the chemicals used in the Examples set forth herein may be obtained from standard commercial sources, where such sources include, for example, Acros Organics (Pittsburgh, Pa.), Sigma-Aldrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," 2nd Ed., Academic Press, New York, 1983; H. O. House, "Modern Synthetic Reactions," 2nd Ed., W. A. Benjamin, Inc. Menlo Park, Calif., 1972; T. L. Glichrist, "Heterocyclic Chemistry," 2nd Ed. John Wiley and Sons, New York, 1992; J. March, "Advanced Organic Chemistry: reactions, Mechanisms and Structure," 5th Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as those listed above) provide custom synthesis services.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have one heteroatom, or 1-2 heteroatoms, or 1-3 heteroatoms, or 1-4 heteroatoms.

In one aspect the heteroalkyl chain contains from 1 to 18 (i.e., 1-18) member atoms (carbon and heteroatoms), and in various embodiments contain 1-12, or 1-6, or 1-4 member atoms.

Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have, e.g., 1-2 substituents, or 1-3 substituents, or 1-4 substituents. Exemplary heteroalkyl substituents include esters (—C(O)—O—R) and carbonyls (—C(O)—).

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is $H_2O$.

"Lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

"Lipid particle" means a lipid formulation that can be used to deliver a therapeutic nucleic acid (e.g., mRNA) to a target site of interest (e.g., cell, tissue, organ, and the like). In preferred embodiments, the lipid particle is a nucleic acid-lipid particle, which is typically formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

Lipid particles typically have a mean diameter of from 30 nm to 150 nm, from 40 nm to 150 nm, from 50 nm to 150 nm, from 60 nm to 130 nm, from 70 nm to 110 nm, from 70 nm to 100 nm, from 80 nm to 100 nm, from 90 nm to 100 nm, from 70 to 90 nm, from 80 nm to 90 nm, from 70 nm to 80 nm, or 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

"Lipid encapsulated" can mean a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

"Lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

"Amphipathic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

"Neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

"Non-cationic lipid" means an amphipathic lipid or a neutral lipid or anionic lipid, and is described in more detail below.

"Anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-B1 1).

The term "substituted" means substitution with specified groups other than hydrogen, or with one or more groups, moieties, or radicals which can be the same or different, with each, for example, being independently selected.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof. "Antisense RNA" is an RNA strand having a sequence complementary to a target gene mRNA, that can induce RNAi by binding to the target gene mRNA. "Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form iNA. These antisense and sense RNAs have been conventionally synthesized with an RNA synthesizer.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

By "RNA" is meant a molecule comprising at least one ribonucleotide residue. By "ribonucleotide" is meant a nucleotide with a hydroxyl group at the 2' position of a γ-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of an interfering RNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

By "nucleotide" as used herein is as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (i.e. join by hydrogen bonding) with each other. By "complementary" is meant that a nucleic acid can form hydrogen bond(s) with another nucleic acid sequence either by traditional Watson-Crick or by other non-traditional modes of binding.

MicroRNAs (miRNA) are single-stranded RNA molecules of 21-23 nucleotides in length, which regulate gene expression miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression As used herein the term "small interfering RNA (siRNA)", sometimes known as short interfering RNA or silencing RNA, is used to refer to a class of double-stranded RNA molecules, 16-40 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

As used herein, the term RNAi refers to an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

What are described herein are compounds of formula I, II, III, and IV.

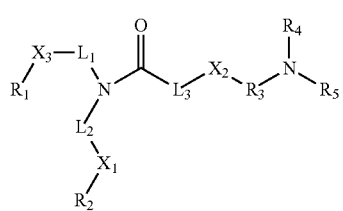

in which $R_1$ and $R_2$ both consist of a linear alkyl consisting of 1 to 9 carbons, an alkenyl or alkynyl consisting of 2 to 11 carbons;

$L_1$ and $L_2$ both consist of a linear alkylene or alkenylene consisting of 5 to 18 carbons, or forming a heterocycle with N;

$X_1$ and $X_3$ both consist of —CO—O—;

$X_2$ is S or O;

$L_3$ consists of a bond or a linear alkylene consisting of 1 to 6 carbons, or forming a heterocycle with N;

$R_3$ consists of a linear or branched alkylene consisting of 1 to 6 carbons; and $R_4$ and $R_5$ are the same or different, consisting of a hydrogen or a linear or branched alkyl consisting of 1 to 6 carbons, or pharmaceutically acceptable salts thereof.

What are also described herein are any of the compounds listed in ATX-001 to ATX-017, ATX-021 to ATX-023, and ATX-026 to ATX-030 listed in Table 1, below, or a pharmaceutically acceptable salt thereof, in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a nucleic acid. The nucleic acid preferably has an activity of suppressing the expression of the target gene by utilizing RNA interference (RNAi). The lipid composition preferably further comprises a nucleic acid and a neutral lipid or a polymer. The lipid composition preferably encapsulates the nucleic acid.

What is also described herein is a compound of Formula II

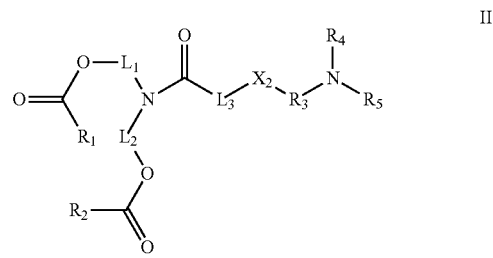

in which $R_1$ and $R_2$ both consist of a linear alkyl consisting of 1 to 12 carbons, an alkenyl or alkynyl consisting of 2 to 12 carbons, $L_1$ and $L_2$ both consist of a linear alkylene or alkenylene consisting of 5 to 18 carbons, or forming a heterocycle with N, X is S, $L_3$ is a bond or a linear alkylene consisting of 1 to 6 carbons, or forming a heterocycle with N, $R_3$ is a linear or branched alkylene consisting of 1 to 6 carbons, and $R_4$ and $R_5$ are the same or different, each a hydrogen or a linear or branched alkyl consisting of 1 to 6 carbons; or a pharmaceutically acceptable salt.

In one embodiment of the compound of formula II, $L_1$ and $L_2$ both consist of a linear alkylene consisting of five carbons. In another embodiment of the compound of formula I, $R_3$ is ethylene or propylene. In another embodiment of the compound of formula I, $R_4$ and $R_5$ are the same or different, each hydrogen, methyl, or ethyl. In another embodiment of the compound of formula I, $L_3$ is a bond. In another embodiment of the compound of formula I, $R_1$ and $R_2$ both consist of a linear alkenyl consisting of ten carbons. In another embodiment of the compound of formula I, the compound consists of a compound selected from formulas 1 to 12.

| Number | Structure |
|---|---|
| 1 | 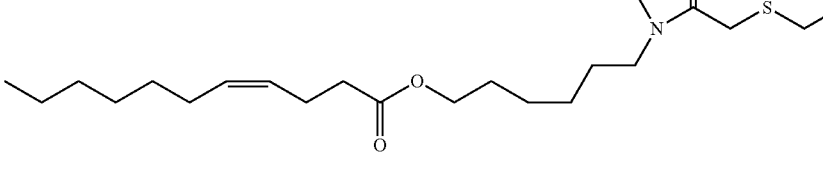 |
| 2 | 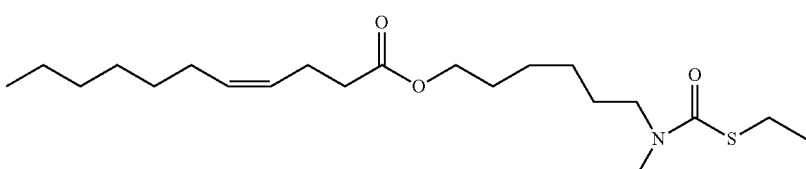 |
| 3 | 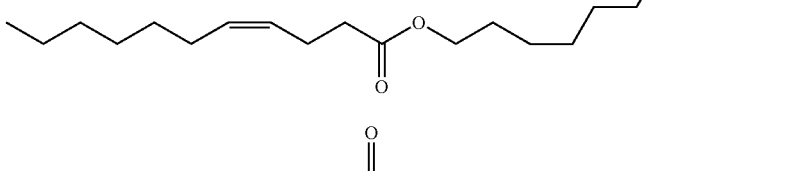 |
| 4 | 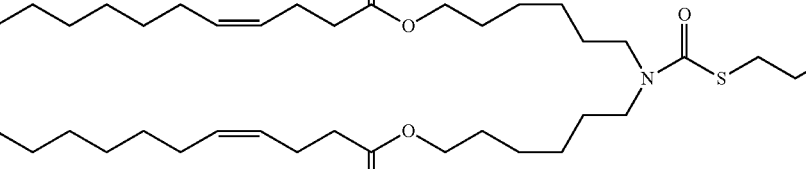 |
| 5 | 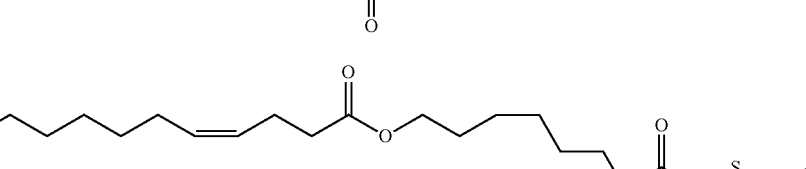 |
| 6 | 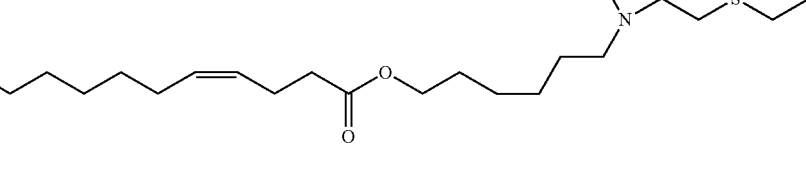 |

-continued

| Number | Structure |
|---|---|
| 7 | 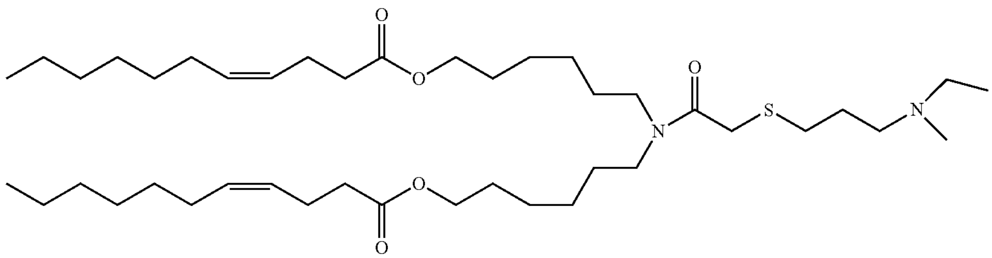 [SMILES: CCCCCC/C=C\CCC(=O)OCCCCCCN(CCCCCCOC(=O)CC/C=C\CCCCCC)C(=O)CSCCCN(C)CC] |
| 8 | 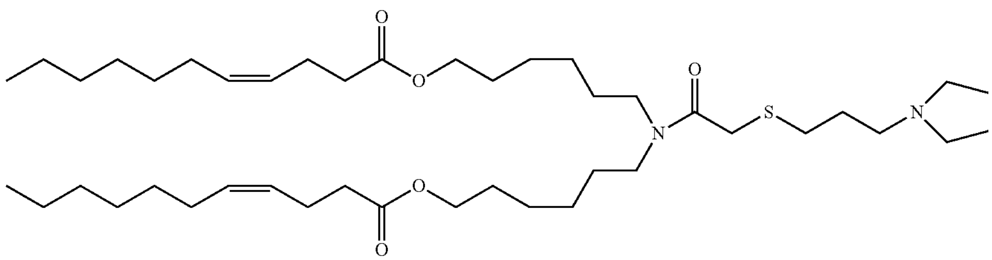 [SMILES: CCCCCC/C=C\CCC(=O)OCCCCCCN(CCCCCCOC(=O)CC/C=C\CCCCCC)C(=O)CSCCCN(CC)CC] |
| 9 | 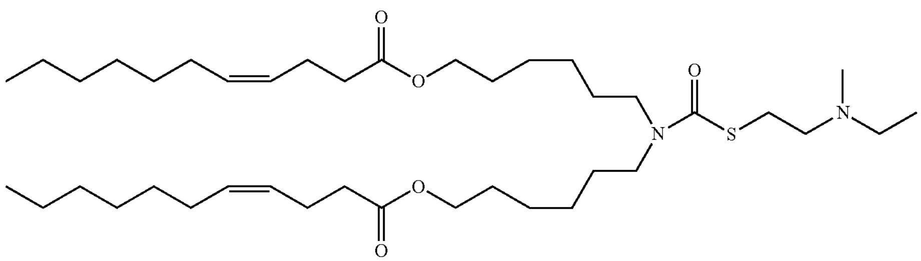 [SMILES: CCCCCC/C=C\CCC(=O)OCCCCCCN(CCCCCCOC(=O)CC/C=C\CCCCCC)C(=O)SCCN(C)CC] |
| 10 | 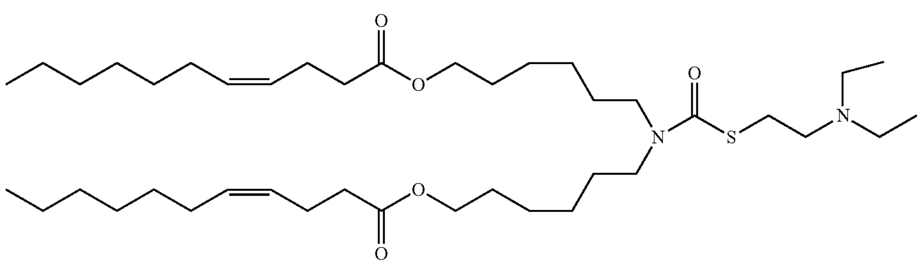 [SMILES: CCCCCC/C=C\CCC(=O)OCCCCCCN(CCCCCCOC(=O)CC/C=C\CCCCCC)C(=O)SCCN(CC)CC] |
| 11 | 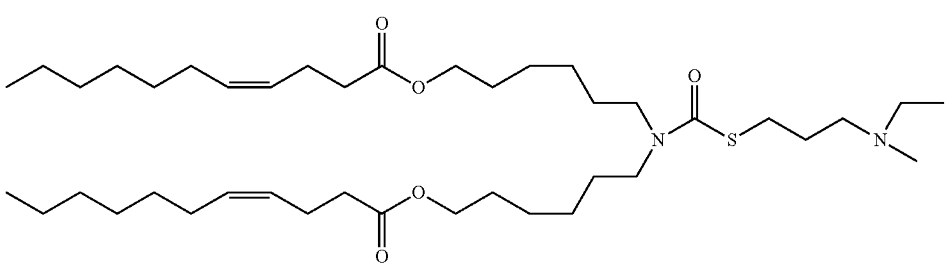 [SMILES: CCCCCC/C=C\CCC(=O)OCCCCCCN(CCCCCCOC(=O)CC/C=C\CCCCCC)C(=O)SCCCN(C)CC] |
| 12 | 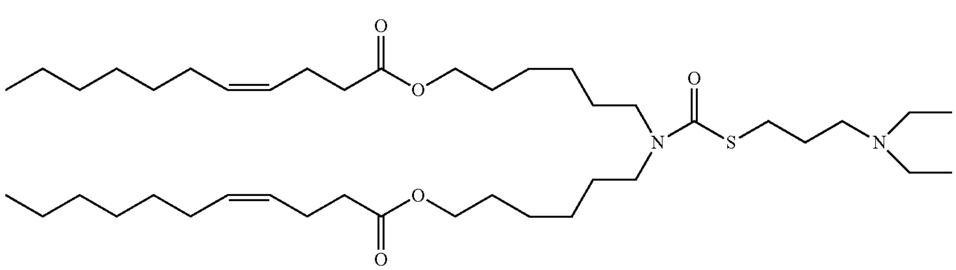 [SMILES: CCCCCC/C=C\CCC(=O)OCCCCCCN(CCCCCCOC(=O)CC/C=C\CCCCCC)C(=O)SCCCN(CC)CC] |

What is also described herein is a compound of formula III or IV

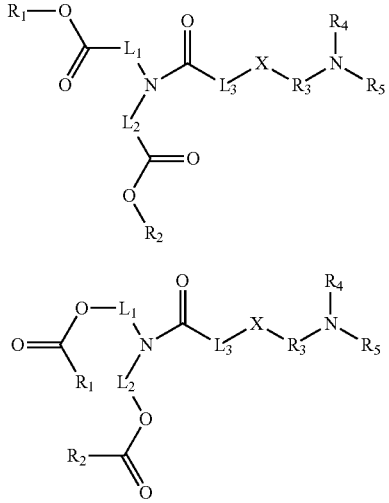

wherein
$R_1$ consists of a branched alkyl with 12 to 20 carbons,
$R_2$ consists of a linear alkyl with 5 to 10 carbons or a branched alkyl with 12 to 20 carbons,
$L_1$ and $L_2$ each consists of a bond or a linear alkyl having 1 to 3 carbons,
X consists of S or O,
$L_3$ consists of a bond or a lower alkyl,
$R_3$ consists of a lower alkyl, and
$R_4$ and $R_5$ are the same or different, each consisting of a lower alkyl;
or a pharmaceutically acceptable salt thereof.

In one embodiment of the compound of formula III or IV, $L_3$ consists of a bond. Another embodiment of the compound of formula III or IV, X is S. In another embodiment the compound of formula III or IV, $R_3$ is ethylene. In another embodiment of the compound of formula III or IV, $R_3$ is n-propylene or isopropylene. In another embodiment of the compound of formula III or IV, $R_4$ and $R_5$ are separately methyl, ethyl, or isopropyl. In another embodiment of the compound of formula III or IV, $L_1$ and $L_2$ each consists of a bond. In another embodiment of the compound of formula III or IV, $L_1$ and $L_2$ consist of a methylene. In another embodiment of the compound of formula III or IV, $R_1$ and $R_2$ each consist of branched alkyl. In another embodiment of the compound of formula III or IV, $R_2$ consists of an alkyl. In another embodiment of the compound of formula III or IV, $R_1$ and $R_2$ each consists of 19 or 20 carbons. In another embodiment of the compound of formula III or IV, $R_1$ or $R_2$ each consists of 13 or 14 carbons. In another embodiment of the compound of formula III or IV, $L_3$ is methylene, $R_3$ is ethylene, $X_2$ is S, and $R_4$ and $R_5$ are each methyl. In another embodiment of the compound of formula III or IV, wherein $L_3$ is a bond, $R_3$ is ethylene, X is S, and $R_4$ and $R_5$ are each methyl. In another embodiment of the compound of formula III or IV, $L_3$ is a bond, $R_3$ is n-propylene, X is S, and $R_4$ and $R_5$ are each methyl. In another embodiment of the compound of formula III or IV, $L_3$ is a bond, $R_3$ is isopropylene, X is S, and $R_4$ and $R_5$ are each methyl. In another embodiment of the compound of formula III or IV, selected from the group consisting of a compound of formula ATX-B-1 to ATX-B-12 as follows.

ATX-B-1
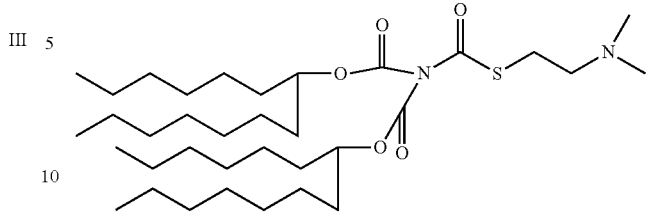

ATX-B-2
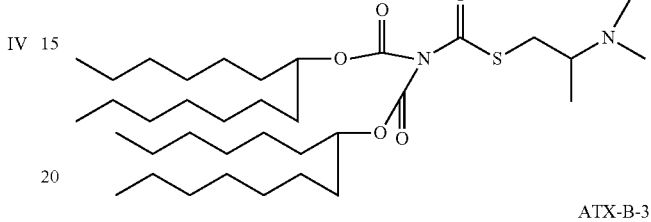

ATX-B-3
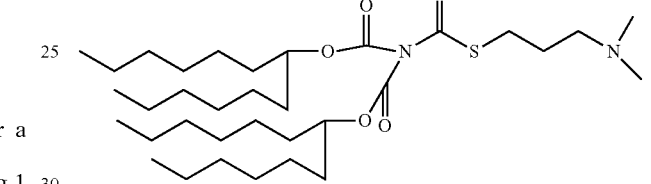

ATX-B-4
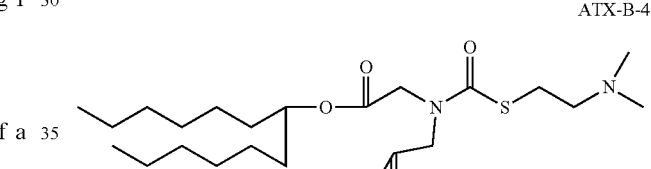

ATX-B-5
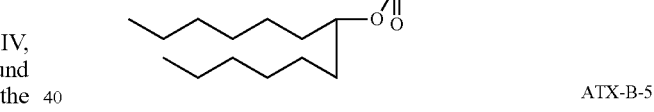

ATX-B-6
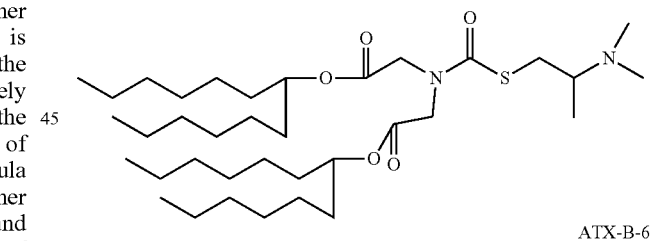

ATX-B-7
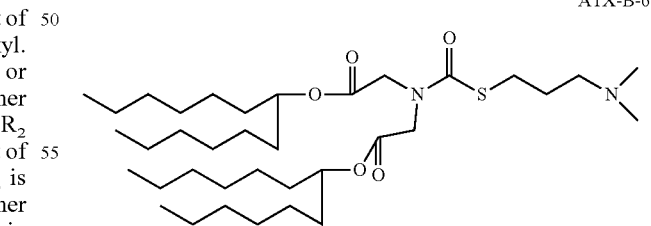

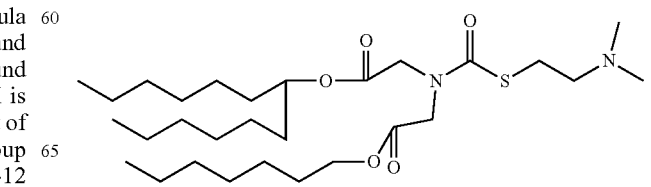

-continued

ATX-B-8
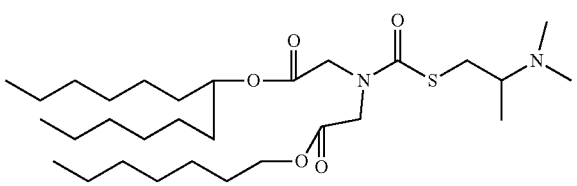

ATX-B-9
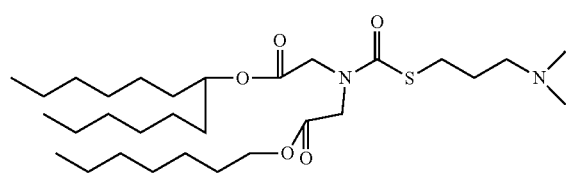

ATX-B-10
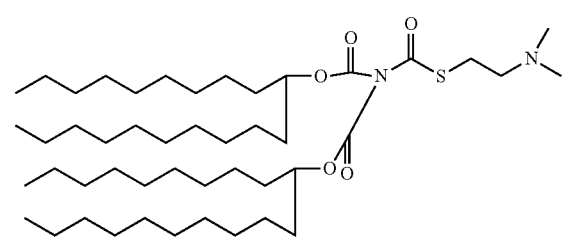

ATX-B-12
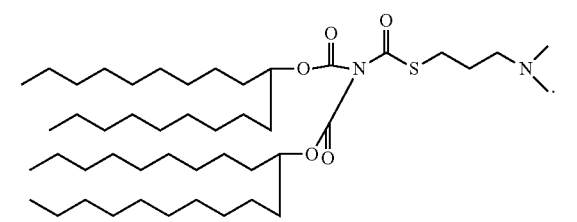

The compounds of formulas I, II, III, and IV form may be a pharmaceutically acceptable salt thereof, in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a nucleic acid. The nucleic acid preferably has an activity of suppressing the expression of the target gene by utilizing RNA interference (RNAi). The lipid composition preferably further comprises a nucleic acid and a neutral lipid or a polymer. The lipid composition preferably encapsulates the nucleic acid.

Reference to compounds of formulas I, II, III, and IV herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when compounds of formulas I, II, III, and IV contain both a basic moiety, such as, but not limited to, a pyridine or imidazole, and an acidic moiety, such as, but not limited to, a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of formulas I, II, III, and IV may be formed, for example, by reacting compounds of formulas I, II, III, and IV with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, *J. Pharmaceutical Sciences* (1977) 66(1)1-19; P. Gould, International *J. Pharmaceutics* (1986) 33 201-217; Anderson et al., The Practice of Medicinal Chemistry (1996), Academic Press, New York; and in The Orange Book (Food & Drug Administration, Washington, D.C. on their website). These disclosures are incorporated by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine or lysine. Basic nitrogen-containing groups may be quartemized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds of formulas I, II, III, and IV for purposes of the disclosure.

Compounds of formulas I, II, III, and IV can exist in unsolvated and solvated forms, including hydrated forms. In general, the solvated forms, with pharmaceutically acceptable solvents such as water, ethanol, and the like, are equivalent to the unsolvated forms for the purposes of this disclosure.

Compounds of formulas I, II, III, and IV and salts, solvates thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compounds of formulas I, II, III, and IV are within the scope of this disclosure).

All stereoisomers (for example, geometric isomers, optical isomers, and the like) of the present compounds (including those of the salts, solvates, and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", and the like, is intended to equally apply to the salt and solvate of enantiomers, stereoisomers, rotamers, tautomers, racemates, or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Lipid Particles

The description provides lipid particles comprising one or more therapeutic mRNA molecules encapsulated within the lipid particles.

In some embodiments, the mRNA is fully encapsulated within the lipid portion of the lipid particle such that the mRNA in the lipid particle is resistant in aqueous solution to nuclease degradation. In other embodiments, the lipid particles described herein are substantially non-toxic to mammals such as humans. The lipid particles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid particles of the invention also typically have a lipid:RNA ratio (mass/mass ratio) of from 1:1 to 100:1, from 1:1 to 50:1, from 2:1 to 25:1, from 3:1 to 20:1, from 5:1 to 15:1, or from 5:1 to 10:1, or from 10:1 to 14:1, or from 9:1 to 20:1. In one embodiment, the lipid particles have a lipid: RNA ratio (mass/mass ratio) of 12:1. In another embodiment, the lipid particles have a lipid: mRNA ratio (mass/mass ratio) of 13:1.

In preferred embodiments, the lipid particles comprise an mRNA, a cationic lipid (e.g., one or more cationic lipids or salts thereof described herein), a phospholipid, and a conjugated lipid that inhibits aggregation of the particles (e.g., one or more PEG-lipid conjugates). The lipid particles can also include cholesterol. The lipid particles may comprise at least 1, 2, 3, 4, 5, 6, 7, 8, 9, 10, or more mRNA that express one or more polypeptides.

In the nucleic acid-lipid particles the mRNA may be fully encapsulated within the lipid portion of the particle, thereby protecting the nucleic acid from nuclease degradation. In preferred embodiments, a lipid particle comprising an mRNA is fully encapsulated within the lipid portion of the particle, thereby protecting the nucleic acid from nuclease degradation. In certain instances, the mRNA in the lipid particle is not substantially degraded after exposure of the particle to a nuclease at 37° C. for at least 20, 30, 45, or 60 minutes. In certain other instances, the mRNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the mRNA is complexed with the lipid portion of the particle. One of the benefits of the formulations of the present invention is that the nucleic acid-lipid particle compositions are substantially non-toxic to mammals such as humans.

"Fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a liposomal formulation, measuring the resulting fluorescence, and comparing it to the fluorescence observed upon addition of a small amount of nonionic detergent.

Detergent-mediated disruption of the liposomal bilayer releases the encapsulated nucleic acid, allowing it to interact with the membrane-impermeable dye. Nucleic acid encapsulation may be calculated as $E=(I_0-I)/I_0$, where/and $I_0$ refers to the fluorescence intensities before and after the addition of detergent.

In other embodiments, the present invention provides a nucleic acid-lipid particle composition comprising a plurality of nucleic acid-lipid particles.

The lipid particle comprises mRNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the mRNA encapsulated therein.

Depending on the intended use of the lipid particles, the proportions of the components can be varied and the delivery efficiency of a particular formulation can be measured using assays know in the art.

Cationic Lipids

The description includes synthesis of certain cationic lipid compounds. The compounds are particularly suitable for delivering polynucleotides to cells and tissues as demonstrated in subsequent sections. The lipomacrocycle compound described herein may be used for other purposes as well as, for example, recipients and additives.

The synthetic methods for the cationic lipid compounds can be synthesized with the skills in the art. The skilled of the art will recognize other methods to produce these compounds, and to produce also the other compounds of the description.

The cationic lipid compounds may be combined with an agent to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The lipomacrocycle compounds may be combined with other cationic lipid compounds, polymers (synthetic or natural), surfactants, cholesterol, carbohydrates, proteins, or lipids, to form the particles.

These particles may then optionally be combined with a pharmaceutical excipient to form a pharmaceutical composition.

The present description provides novel cationic lipid compounds and drug delivery systems based on the use of such cationic lipid compounds. The system may be used in the pharmaceutical/drug delivery arts to deliver polynucleotides, proteins, small molecules, peptides, antigen, or drugs, to a patient, tissue, organ, or cell. These novel compounds may also be used as materials for coating, additives, excipients, materials, or bioengineering.

The cationic lipid compounds of the present description provide for several different uses in the drug delivery art. The amine-containing portion of the cationic lipid compounds may be used to complex polynucleotides, thereby enhancing the delivery of polynucleotide and preventing their degradation. The cationic lipid compounds may also be used in the formation of picoparticles, nanoparticles, microparticles, liposomes, and micelles containing the agent to be delivered. Preferably, the cationic lipid compounds are biocompatible and biodegradable, and the formed particles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

In certain embodiments, the cationic lipid compounds are relatively non-cytotoxic. The cationic lipid compounds may be biocompatible and biodegradable. The cationic lipid may have a $pK_a$ in the range of approximately 5.5 to approximately 7.5, more preferably between approximately 6.0 and approximately 7.0. It may be designed to have a desired $pK_a$ between approximately 3.0 and approximately 9.0, or between approximately 5.0 and approximately 8.0. The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the agent to be delivered, they can be synthesized from commercially available starting materials; and/or they are pH responsive and can be engineered with a desired $pK_a$.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5-10% phospholipid, and 1-10% PEG. The composition may contain 60-70% cationic lipid compound, 25-35% cholesterol, and 5-10% PEG. The composition may contain up to 90% cationic lipid compound and 2-15% helper lipid.

The formulation may be a lipid particle formulation, for example containing 8-30% compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Non-cationic Lipids

The non-cationic lipids that are used in lipid particles can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the non-cationic lipid present in lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, dioctadecyldimethyl ammonium bromide, ceramide, and sphingomyelin.

In some embodiments, the non-cationic lipid comprises from 10 mol % to 60 mol %, from 20 mol % to 55 mol %, from 20 mol % to 45 mol %, 20 mol % to 40 mol %, from 25 mol % to 50 mol %, from 25 mol % to 45 mol %, from 30 mol % to 50 mol %, from 30 mol % to 45 mol %, from 30 mol % to 40 mol %, from 35 mol % to 45 mol %, from 37 mol % to 42 mol %, or 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to 40 mol %, 45 mol %, 50 mol %, 55 mol %, or 60 mol % of the total lipid present in the particle.

In some embodiments, the phospholipid component in the mixture may comprise from 2 mol % to 20 mol %, from 2 mol % to 15 mol %, from 2 mol % to 12 mol %, from 4 mol % to 15 mol %, or from 4 mol % to 10 mol % (or any fraction thereof or range therein) of the total lipid present in the particle. In certain preferred embodiments, the phospholipid component in the mixture comprises from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

In other embodiments, the cholesterol component in the mixture may comprise from 25 mol % to 45 mol %, from 25 mol % to 40 mol %, from 30 mol % to 45 mol %, from 30 mol % to 40 mol %, from 27 mol % to 37 mol %, from 25 mol % to 30 mol %, or from 35 mol % to 40 mol % (or any fraction thereof or range therein) of the total lipid present in the particle. In certain preferred embodiments, the cholesterol component in the mixture comprises from 25 mol % to 35 mol %, from 27 mol % to 35 mol %, from 29 mol % to 35 mol %, from 30 mol % to 35 mol %, from 30 mol % to 34 mol %, from 31 mol % to 33 mol %, or 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from 25 mol % to 45 mol %, from 25 mol % to 40 mol %, from 30 mol % to 45 mol %, from 30 mol % to 40 mol %, from 31 mol % to 39 mol %, from 32 mol % to 38 mol %, from 33 mol % to 37 mol %, from 35 mol % to 45 mol %, from 30 mol % to 35 mol %, from 35 mol % to 40 mol %, or 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle.

In other embodiments, the non-cationic lipid comprises from 5 mol % to 90 mol %, from 10 mol % to 85 mol %, from 20 mol % to 80 mol %, 10 mol % (e.g., phospholipid only), or 60 mol % (e.g., phospholipid and cholesterol or derivative thereof) (or any fraction thereof or range therein) of the total lipid present in the particle.

The percentage of non-cationic lipid present in the lipid particles is a target amount, and that the actual amount of non-cationic lipid present in the formulation may vary, for example, by ±5 mol %.

Lipid Conjugates

In addition to cationic, the lipid particles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof.

In a preferred embodiment, the lipid conjugate is a PEG-lipid. Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights; and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$).

The PEG moiety of the PEG-lipid conjugates described herein may comprise an average molecular weight ranging from 550 daltons to 10,000 daltons. In certain instances, the PEG moiety has an average molecular weight of from 750 daltons to 5,000 daltons (e.g., from 1,000 daltons to 5,000 daltons, from 1,500 daltons to 3,000 daltons, from 750 daltons to 3,000 daltons, from 750 daltons to 2,000 daltons). In preferred embodiments, the PEG moiety has an average molecular weight of 2,000 daltons or 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (-0-), succinyl (-(0)CCH$_2$CH$_2$C(0)-), succinamidyl (—NHC(0)CH$_2$CH$_2$C(0)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl).

The term "dialkyloxypropyl" or "DAA" includes a compound having 2 alkyl chains, R and R, both of which have independently between 2 and 30 carbons. The alkyl groups can be saturated or have varying degrees of unsaturation.

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of 750 or 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from 0.1 mol % to 2 mol %, from 0.5 mol % to 2 mol %, from 1 mol % to 2 mol %, from 0.6 mol % to 1.9 mol %, from 0.7 mol % to 1.8 mol %, from 0.8 mol % to 1.7 mol %, from 0.9 mol % to 1.6 mol %, from 0.9 mol % to 1.8 mol %, from 1 mol % to 1.8 mol %, from 1 mol % to 1.7 mol %, from 1.2 mol % to 1.8 mol %, from 1.2 mol % to 1.7 mol %, from 1.3 mol % to 1.6 mol %, or from 1.4 mol % to 1.5 mol % (or any fraction thereof or range therein) of the total lipid present in the particle. In other embodiments, the lipid conjugate (e.g., PEG-lipid) comprises from 0 mol % to 20 mol %, from 0.5 mol % to 20 mol %, from 2 mol % to 20 mol %, from 1.5 mol % to 18 mol %, from 2 mol % to 15 mol %, from 4 mol % to 15 mol %, from 2 mol % to 12 mol %, from 5 mol % to 12 mol %, or 2 mol % (or any fraction thereof or range therein) of the total lipid present in the particle.

In further embodiments, the lipid conjugate (e.g., PEG-lipid) comprises from 4 mol % to 10 mol %, from 5 mol % to 10 mol %, from 5 mol % to 9 mol %, from 5 mol % to 8 mol %, from 6 mol % to 9 mol %, from 6 mol % to 8 mol %, or 5 mol %, 6 mol %, 7 mol %, 8 mol %, 9 mol %, or 10 mol % (or any fraction thereof or range therein) of the total lipid present in the particle.

The percentage of lipid conjugate (e.g., PEG-lipid) present in the lipid particles of the invention is a target amount, and the actual amount of lipid conjugate present in the formulation may vary, for example, by ±2 mol %. One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. In addition, other variables including, e.g., pH, temperature, or ionic strength, can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Compositions and Formulations for Administration

The nucleic acid-lipid compositions of this disclosure may be administered by various routes, for example, to effect systemic delivery via intravenous, parenteral, intraperitoneal, or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic, a cationic lipid, an amphiphile, a phospholipid, cholesterol, and a PEG-linked cholesterol may be administered to a subject having a disease or disorder associated with expression or overexpression of a gene that can be reduced, decreased, downregulated, or silenced by the composition.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin, or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in either a liquid or solid form. Preferred systems for dispensing liquids as a nasal spray are disclosed in U.S. Pat. No. 4,511,069. Such formulations may be conveniently prepared by dissolving compositions according to the present disclosure in water to produce an aqueous solution, and rendering said solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien ed., Elsevier Publishers, New York, 1985; and in U.S. Pat. No. 4,778,810. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally formulated with a surface active agent, such as a nonionic surfactant (e.g., polysorbate-80), and one or more buffers. In some embodiments of the present disclosure, the nasal spray solution further comprises a propellant. The pH of the nasal spray solution may be from pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this disclosure is a pharmaceutical product which includes a solution containing a composition of this disclosure and an actuator for a pulmonary, mucosal, or intranasal spray or aerosol.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet, or gel.

To formulate compositions for pulmonary delivery within the present disclosure, the biologically active agent can be combined with various pharmaceutically acceptable additives, as well as a base or carrier for dispersion of the active agent(s). Examples of additives include pH control agents such as arginine, sodium hydroxide, glycine, hydrochloric acid, citric acid, and mixtures thereof. Other additives include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly(hydroxybutyric acid-glycolic acid) copolymer, and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, crosslinking, and the like. The carrier can be provided in a variety of forms, including fluid or viscous solutions, gels, pastes, powders, microspheres, and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3,000. Examples of hydrophilic low molecular weight compounds include polyol compounds, such as oligo-, di- and monosaccharides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time release formulation, for example in a composition which includes a slow release polymer. The active agent can be prepared with carriers that will protect against rapid release, for example a controlled release vehicle such as a polymer, microencapsulated delivery system, or bioadhesive gel. Prolonged delivery of the active agent, in various compositions of the disclosure can be brought about by including in the composition agents that delay absorption, for example, aluminum monosterate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications, and equivalents. In particular, this disclosure includes any combination of the features, terms, or elements of the various illustrative components and examples.

EXAMPLES

Example 1

Exemplary compounds of formula I are provided in Table 1.

TABLE 1

| Lipid ID | Novel Lipid | MW | pKa | KD @ 0.3 mg/kg |
|---|---|---|---|---|
| ATX-001 | | 695.1 | 8.9 | ~0 |
| ATX-002 | | 681 | 8.7 | 98 |
| ATX-003 | | 695.1 | 9.3 | ~0 |
| ATX-004 | | 709.13 | 9.4 | ~0 |
| ATX-005 | | 709.13 | 9.0 | ~0 |
| ATX-006 | | 723.15 | 9.8 | ~0 |

TABLE 1-continued

| Lipid ID | Novel Lipid | MW | pKa | KD @ 0.3 mg/kg |
|---|---|---|---|---|
| ATX-007 | | 723.15 | 9.5 | n/a |
| ATX-008 | | 737.18 | 10.3 | n/a |
| ATX-009 | | 695.1 | 8.8 | ~0 |
| ATX-010 | | 709.13 | 9.6 | 30 |
| ATX-011 | | 709.13 | 9.4 | n/a |
| ATX-012 | | 723.15 | 10.2 | ~0 |

TABLE 1-continued
| Lipid ID | Novel Lipid | MW | pKa | KD @ 0.3 mg/kg |
|---|---|---|---|---|
| ATX-013 | 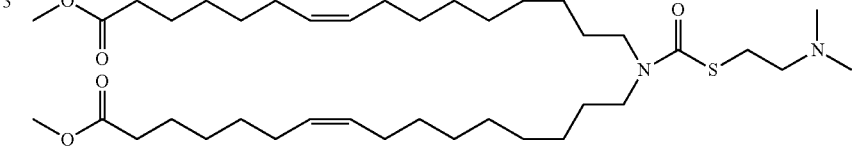 | 681.01 | | n/a |
| ATX-014 | 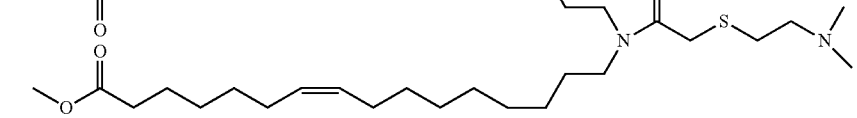 | 695.1 | | n/a |
| ATX-015 | 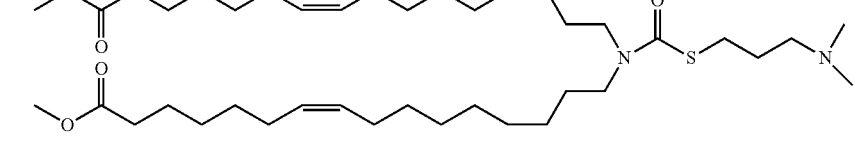 | 695.1 | | n/a |
| ATX-016 | 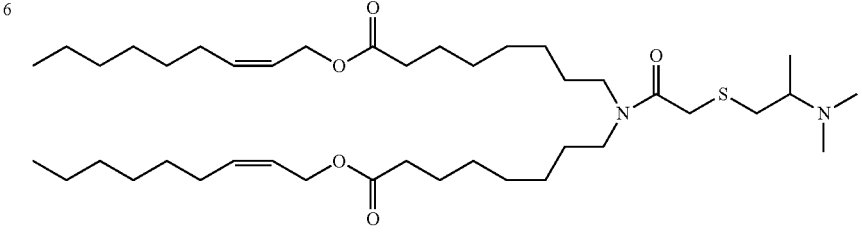 | 709.13 | | 15 |
| ATX-017 | 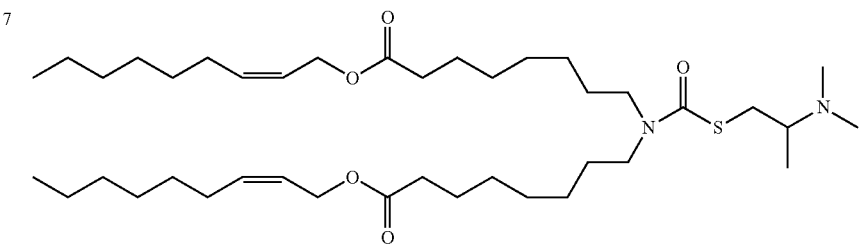 | 695.1 | | n/a |
| ATX-021 | 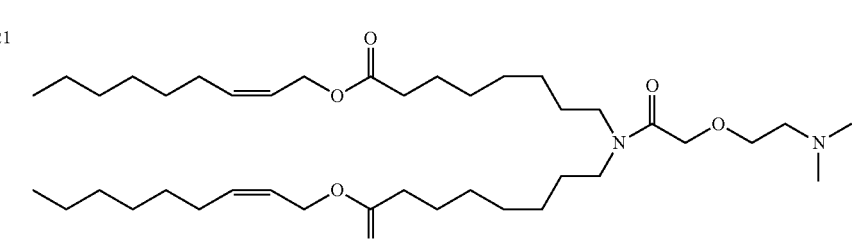 | 679.04 | | n/a |
| ATX-022 | 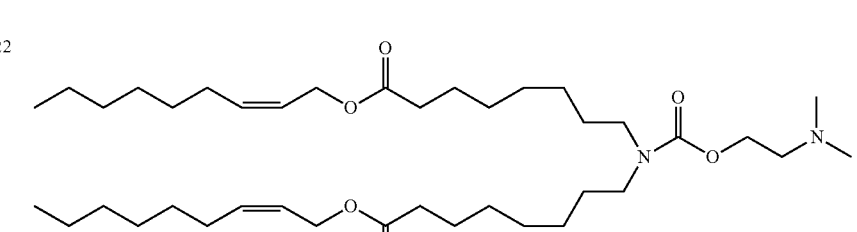 | 665.01 | | n/a |

TABLE 1-continued

| Lipid ID | Novel Lipid | MW | pKa | KD @ 0.3 mg/kg |
|---|---|---|---|---|
| ATX-023 | | 695.1 | | n/a |
| ATX-026 | | 681.07 | | n/a |
| ATX-027 | | 695.1 | | n/a |
| ATX-028 | | 681.07 | | n/a |
| ATX-029 | | 681.1 | | n/a |
| ATX-030 | | 695.1 | | n/a |

Table 1 shows the name and structure of each compound, its molecular weight, its $pK_a$, and its knockdown bioactivity (KD) in an assay described below in Example 19.

Exemplary compounds of formulas II and III are provided in Tables 2, and 3.

TABLE 2
| Number | Structure |
|---|---|
| 1 | 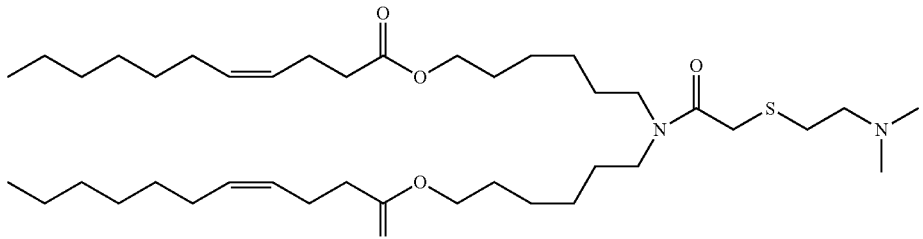 |
| 2 | 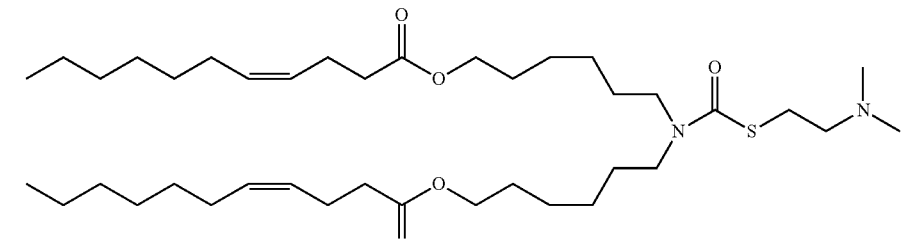 |
| 3 | 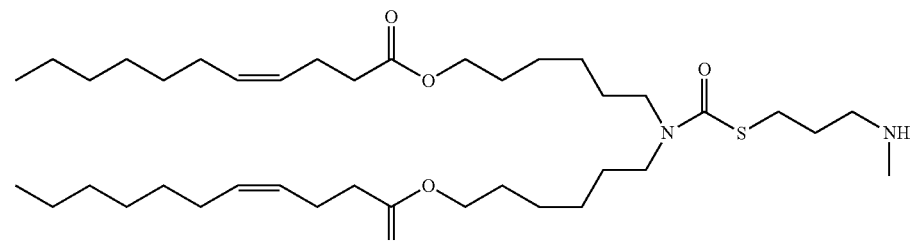 |
| 4 | 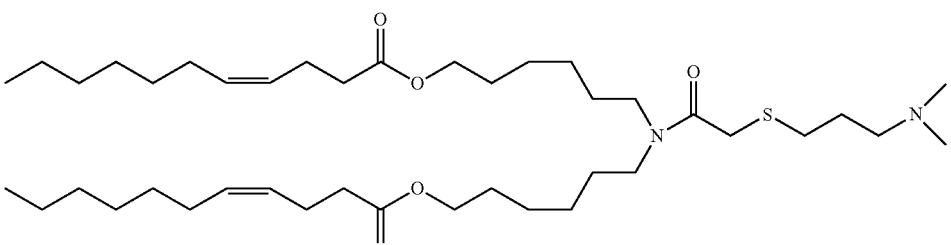 |
| 5 | 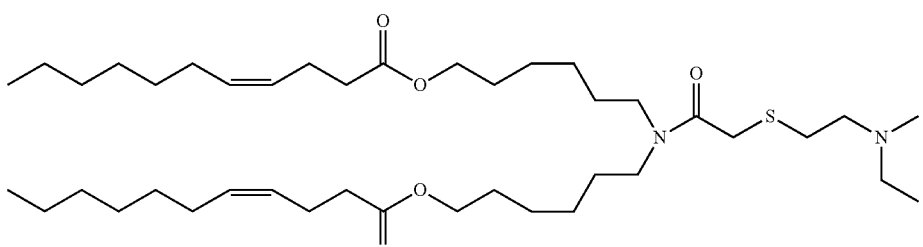 |
| 6 | 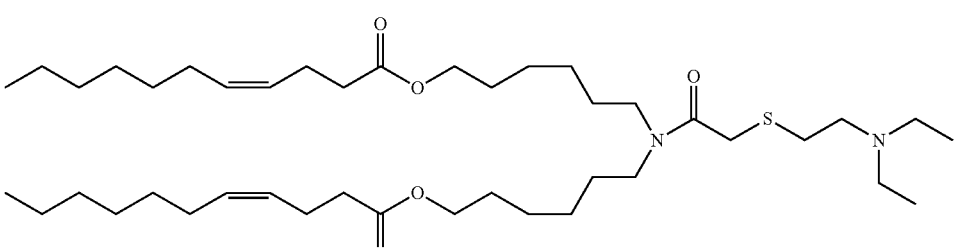 |

TABLE 2-continued
| Number | Structure |
|---|---|
| 7 | 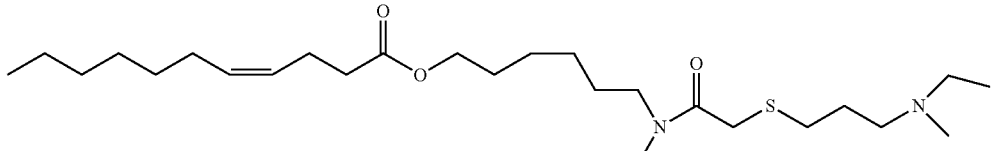 |
| 8 | 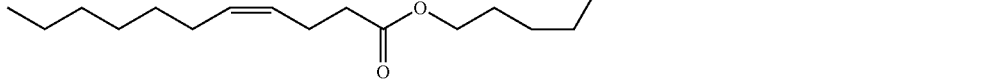 |
| 9 | 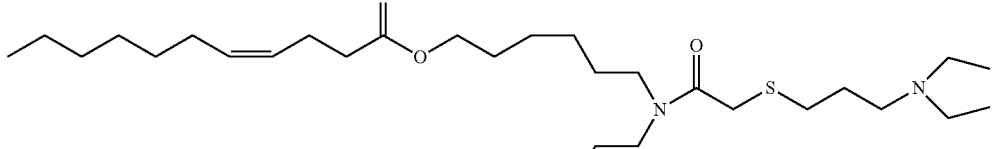 |
| 10 | 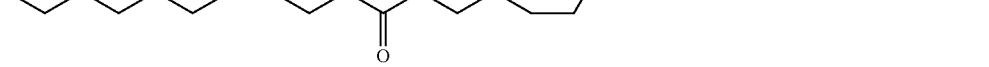 |
| 11 | 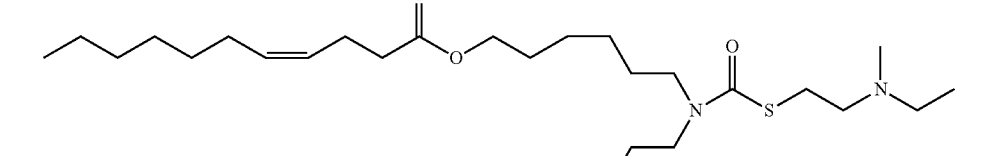 |
| 12 | 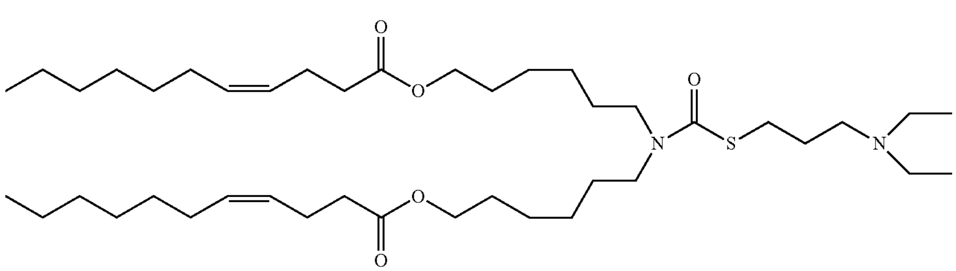 [SMILES: CCCCCC/C=C\CCC(=O)OCCCCCCN(CCCCCCOC(=O)CC/C=C\CCCCCC)C(=O)SCCCN(CC)CC] |

TABLE 3

| Name | Structure |
|------|-----------|
| ATX-B-1 | 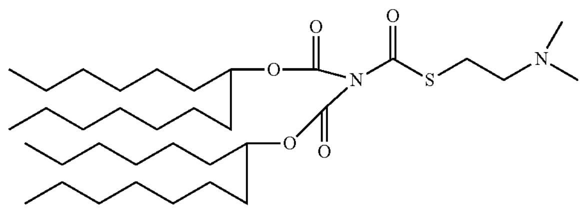 [SMILES: CCCCCCCC(CCCCCC)OC(=O)N(C(=O)OC(CCCCCC)CCCCCCC)C(=O)SCCN(C)C] |
| ATX-B-2 | 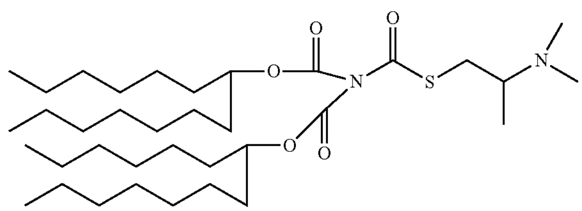 [SMILES: CCCCCCCC(CCCCCC)OC(=O)N(C(=O)OC(CCCCCC)CCCCCCC)C(=O)SCC(C)N(C)C] |
| ATX-B-3 | 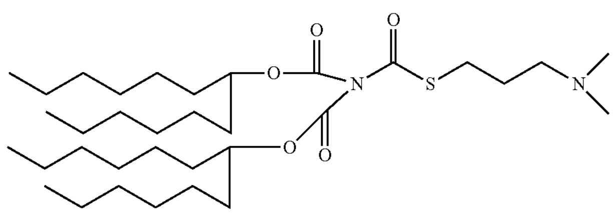 [SMILES: CCCCCCC(CCCCCC)OC(=O)N(C(=O)OC(CCCCCC)CCCCCC)C(=O)SCCCN(C)C] |
| ATX-B-4 | 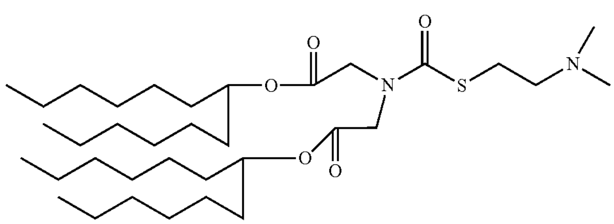 [SMILES: CCCCCCC(CCCCCC)OC(=O)CN(CC(=O)OC(CCCCCC)CCCCCC)C(=O)SCCN(C)C] |
| ATX-B-5 | 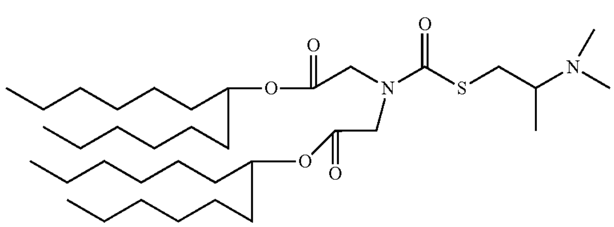 [SMILES: CCCCCCC(CCCCCC)OC(=O)CN(CC(=O)OC(CCCCCC)CCCCCC)C(=O)SCC(C)N(C)C] |
| ATX-B-6 | 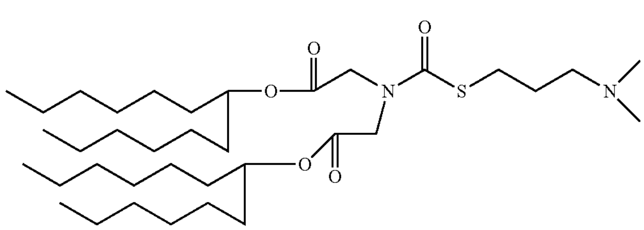 [SMILES: CCCCCCC(CCCCCC)OC(=O)CN(CC(=O)OC(CCCCCC)CCCCCC)C(=O)SCCCN(C)C] |
| ATX-B-7 | 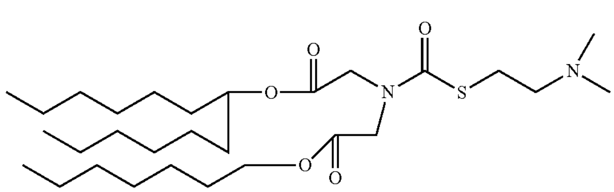 [SMILES: CCCCCCCOC(=O)CN(CC(=O)OC(CCCCCC)CCCCCC)C(=O)SCCN(C)C] |

TABLE 3-continued

| Name | Structure |
|---|---|
| ATX-B-8 | 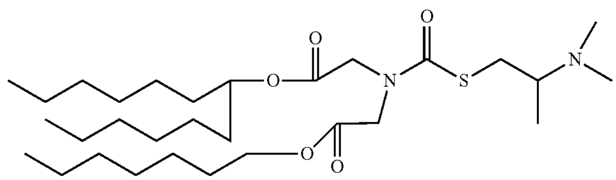 [SMILES: CCCCCCCOC(=O)CN(CC(=O)OC(CCCCCC)CCCCCC)C(=O)SCC(C)N(C)C] |
| ATX-B-9 | 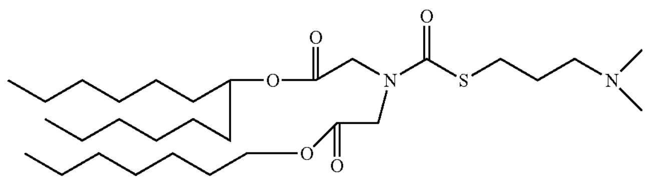 [SMILES: CCCCCCCOC(=O)CN(CC(=O)OC(CCCCCC)CCCCCC)C(=O)SCCCN(C)C] |
| ATX-B-10 | 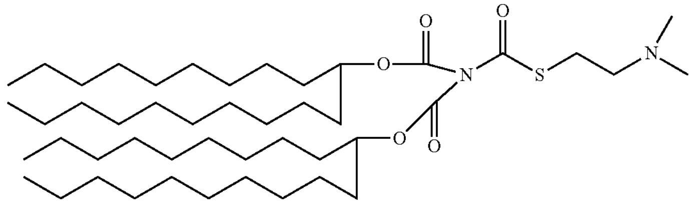 [SMILES: CCCCCCCCCCC(CCCCCCCCC)OC(=O)N(C(=O)OC(CCCCCCCCC)CCCCCCCCCC)C(=O)SCCN(C)C] |
| ATX-B-12 | 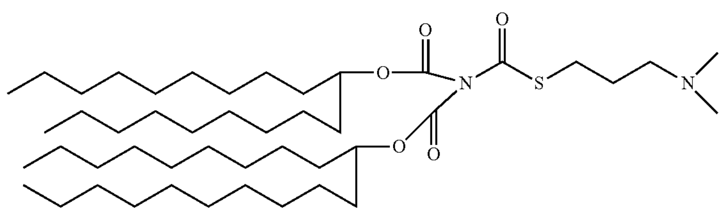 [SMILES: CCCCCCCCCCC(CCCCCCCCC)OC(=O)N(C(=O)OC(CCCCCCCCC)CCCCCCCCC)C(=O)SCCCN(C)C] |

Example 2

Synthesis of methyl 8-bromooctanoate

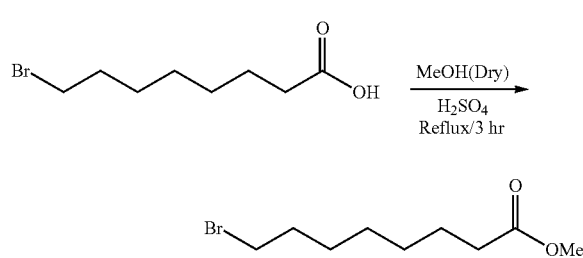

Under N$_2$ atmosphere, 8-bromooctanoic acid was dissolved in dry methanol. Concentrated H$_2$SO$_4$ was added drop-wise and the reaction mixture was stirred under reflux for three hours.

The reaction was monitored by thin layer chromatography until completed. Solvent was completely removed under vacuum. The reaction mixture was diluted with ethyl acetate and washed with water. The water layer was re-extracted with ethyl acetate. The total organic layer was washed with a saturated NaHCO$_3$ solution. The organic layer was washed again with water and finally washed with brine. The product was dried over anhydrous Na$_2$SO$_4$ and concentrated.

Example 3

Synthesis of dimethyl 8,8'-(benzanediyl)dioctanoate

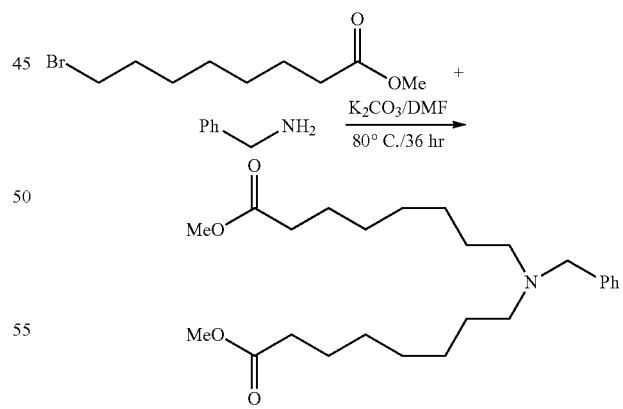

Dry K$_2$CO$_3$ was taken and added to dry dimethylformamide under N$_2$. Benzyl amine in dimethylformamide was slowly added. Methyl 8-bromooctanoate dissolved in dimethylformamide was then added at room temperature. The reaction mixture was heated to 80° C. and the reaction was maintained for 36 hours with stirring.

The reaction was monitored by thin layer chromatography until completed. The reaction product was cooled to room temperature and water was added. The compound was extracted with ethyl acetate. The water layer was re-extracted with ethyl acetate. The total organic layer was washed with water and finally with brine solution. The product was dried over anhydrous Na$_2$SO$_4$ and concentrated.

The reaction product was purified by silica gel column chromatography in 3% methanol in chloroform. 44 grams (g) of pure product was recovered.

Using thin layer chromatograph (TLC) system of 10% methanol in chloroform, the product migrated with a Rf of 0.8, visualizing by charring in ninhydrin. The overall yield was 82%. The compound was a light brown liquid. The structure was confirmed by $^1$H-NMR.

Example 4

Synthesis of dimethyl 8,8'-azanediyldioctanoate

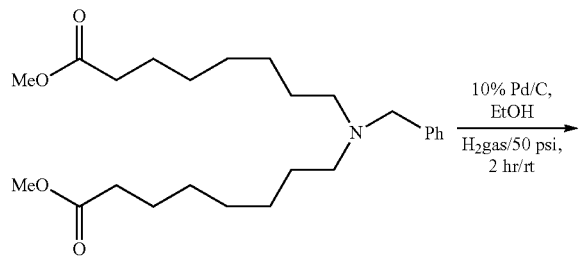

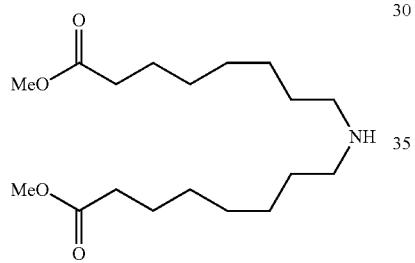

Dimethyl 8,8'-(benzanediyl)dioctanoate was transferred to hydrogenation glass vessel, and ethanol was added followed by 10% Pd/C. The reaction mixture was shaken in a Parr-shaker apparatus under 50 pounds per square inch (psi) H$_2$ atmosphere pressure for two hours at room temperature.

The reaction product was filtered through celite and washed with hot ethyl acetate. The filtrate was concentrated under vacuum.

Example 5

Synthesis of dimethyl 8,8'-((tertbutoxycarbonyl)azanedil) dioctanoate

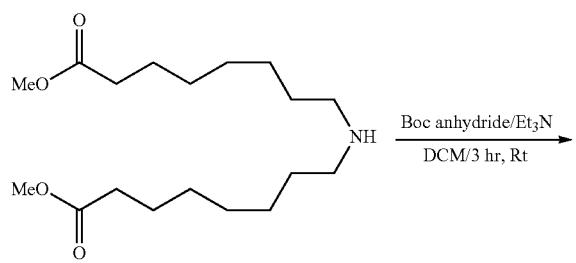

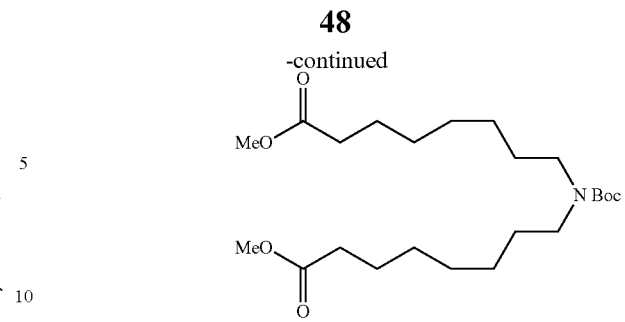

Dimethyl 8,8'-azanediyldioctanoate was transferred to dichloromethane (DCM) and Et$_3$N to the reaction mass and cooled to 0° C. Boc anhydride diluted in DCM was added drop to the above reaction. After the addition was completed, the reaction mixture was stirred at room temperature for three hours.

The reaction was quenched with water and the DCM layer was separated. The water phase was re-extracted with DCM and the combined DCM layers were washed with brine solution and dried with Na$_2$SO$_4$. After concentration, 40 g of crude compound was collected.

Crude reaction product was purified by column chromatography using 0-12% ethyl acetate in hexane. The yield recovered was 48%. A single product migrated by thin layer chromatography in 20% ethyl acetate in hexane with an Rf of 0.5, charring with ninhydrin.

Example 6

Synthesis of 8,8'-((tertbutoxycarbonyl)azanediyl) dioctanoic acid

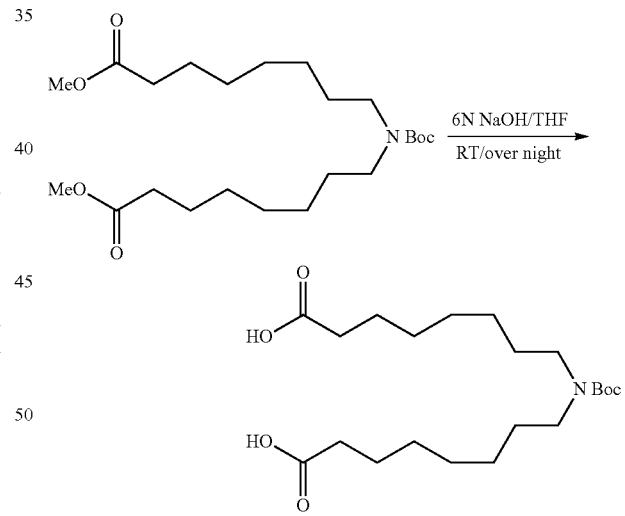

Dimethyl 8,8'-((tertbutoxycarbonyl)azanedil) dioctanoate was transferred to tetrahydrofuran (THF). A 6N sodium hydroxide solution was added at room temperature. The reaction was maintained with stirring overnight at room temperature.

Reaction mass was evaporated under vacuum at 25° C. to remove THF. The reaction product was acidified with 5N HCl. Ethyl acetate was added to the aqueous layer. The separated organic layer was washed with water and the water layer was re-extracted with ethyl acetate. The combined organic layers were washed with brine solution and dried over anhydrous Na$_2$SO$_4$. Concentration of the solution gave 18 g of crude mass.

Example 7

Synthesis of di((Z)-non-2-en-1-yl) 8,8'-((tertbutoxy-carbonyl)azanediyl)

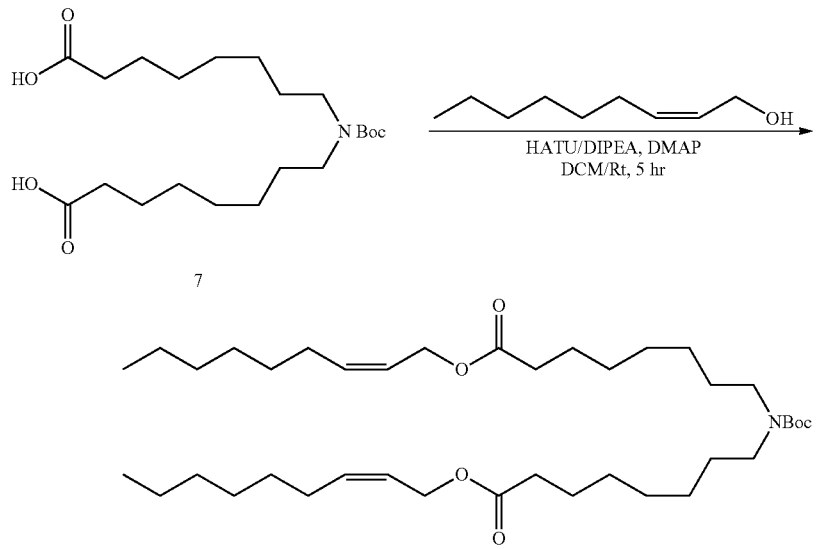

8,8'-((tertbutoxycarbonyl)azanediyl) dioctanoic acid was dissolved in dry DCM. 1-[Bis(dimethylamino)methylene]-1H-1,2,3-triazolo[4,5-b]pyridinium 3-oxid hexafluorophosphate (HATU) was added to this solution. Di-isopropyl ethyl amine was added slowly to the reaction mixture at room temperature. The internal temp rose to 40° C. and a pale yellow color solution was formed. 4-Dimethylaminopyridine (DMAP) was added to the reaction mixture followed by cis-2-nonene-1-ol solution in dry DCM. The reaction changed to brown color. The reaction was stirred for five hours at room temperature.

The reaction was checked by thin layer chromatography under completion. Water was added to the reaction product, which was extracted with DCM. The DCM layer was washed with water followed by brine solution. The organic layer was dried over anhydrous $Na_2SO_4$ and concentrated to obtain 35 g of crude compound.

Example 8

Synthesis of ATX-001

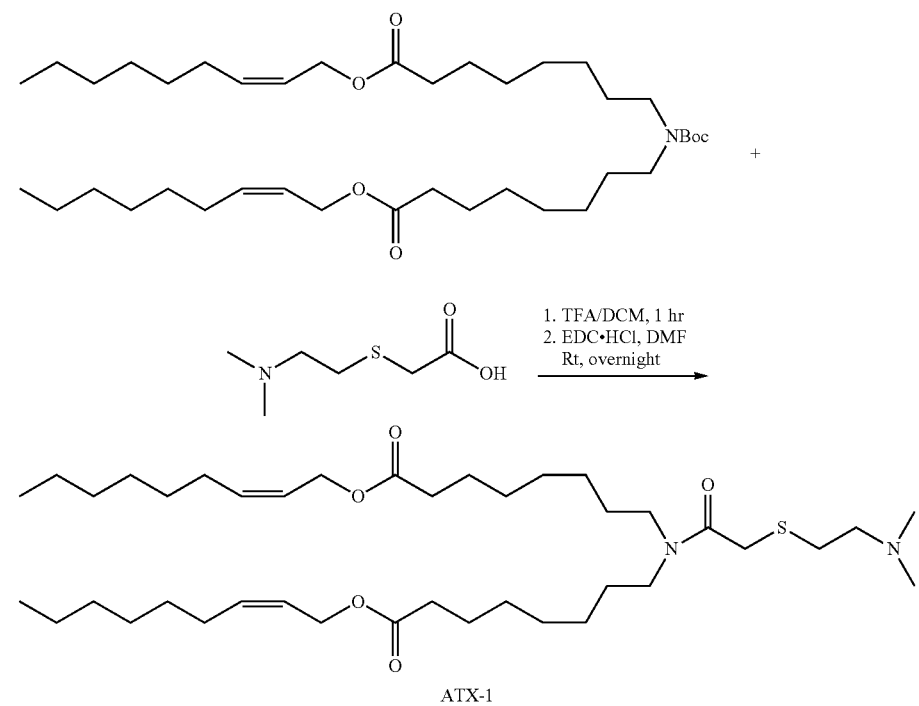

Di((Z)-non-2-en-1-yl) 8,8'((tertbutoxycarbonyl)azanediyl) dioctanoate (0.023 mol, 15 g) was dissolved in dry dichloromethane (DCM) (200 ml). Trifluoroacetic acid (TFA) was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO$_3$ solution. The aqueous layer was re-extracted with DCM, and the combined organic layers were washed with brine solution, dried over Na$_2$SO$_4$ and concentrated. The collected crude product (12 grams) was dissolved in dry DCM (85 ml) under nitrogen gas. Triphosgene were added and the reaction mixture was cooled to 0° C., and Et$_3$N was added drop wise. The reaction mixture was stirred overnight at room temperature. Thin layer chromatography showed that the reaction was completed. DCM solvent was removed from the reaction mass by distillation under N$_2$. The reaction product was cooled to 0° C., diluted with DCM (50 ml), and 2-((2-(dimethylamino)ethyl)thio) acetic acid (0.039 mol, 6.4 g) and carbodiimide (EDC-HCl) (0.054 mol, 10.4 g). The reaction mixture was then stirred overnight at room temperature. Thin layer chromatography showed that the reaction was completed. The reaction product was diluted with 0.3M HCl solution (75 ml), and the organic layer was separated. The aqueous layer was re-extracted with DCM, and the combined organic layers were washed with 10% K$_2$CO$_3$ aqueous solution (75 ml) and dried over anhydrous Na$_2$SO$_4$. Concentration of the solvent gave a crude mass of 10 gram. The crude compound was purified by silica gel column (100-200 mesh) using 3% MeOH/DCM. The yield was 10.5 g (68%).

Example 9

Synthesis of ATX-002

Di((Z)-non-2-en-1-yl) 8,8'((tertbutoxycarbonyl)azanediyl) dioctanoate (13.85 mmol, 9 grams) was dissolved in dry DCM (150 ml). TFA was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO$_3$ solution. The aqueous layer was re-extracted with DCM, and the combined organic layers were washed with brine solution, dried over Na$_2$SO$_4$ and concentrated. The collected crude product was dissolved in dry DCM (85 ml) under nitrogen gas. Triphosgene were added and the reaction mixture was cooled to 0° C., and Et$_3$N was added drop wise. The reaction mixture was stirred overnight at room temperature. Thin layer chromatography showed that the reaction was completed. DCM solvent was removed from the reaction mass by distillation under N$_2$. The reaction product was cooled to 0° C., diluted with DCM (50 ml), and 2-(dimethylamino)ethanethiol HCl (0.063 mol, 8.3 g) was added, followed by Et$_3$N (dry). The reaction mixture was then stirred overnight at room temperature. Thin layer chromatography showed that the reaction was completed. The reaction product was diluted with 0.3M HCl solution (75 ml), and the organic layer was separated. The aqueous layer was re-extracted with DCM, and the combined organic layers were washed with 10% K$_2$CO$_3$ aqueous solution (75 ml) and dried over anhydrous Na$_2$SO$_4$. Concentration of the solvent gave a crude mass of 10 gram. The crude compound was purified by silica gel column (100-200 mesh) using 3% MeOH/DCM. The yield was 3.1 gram.

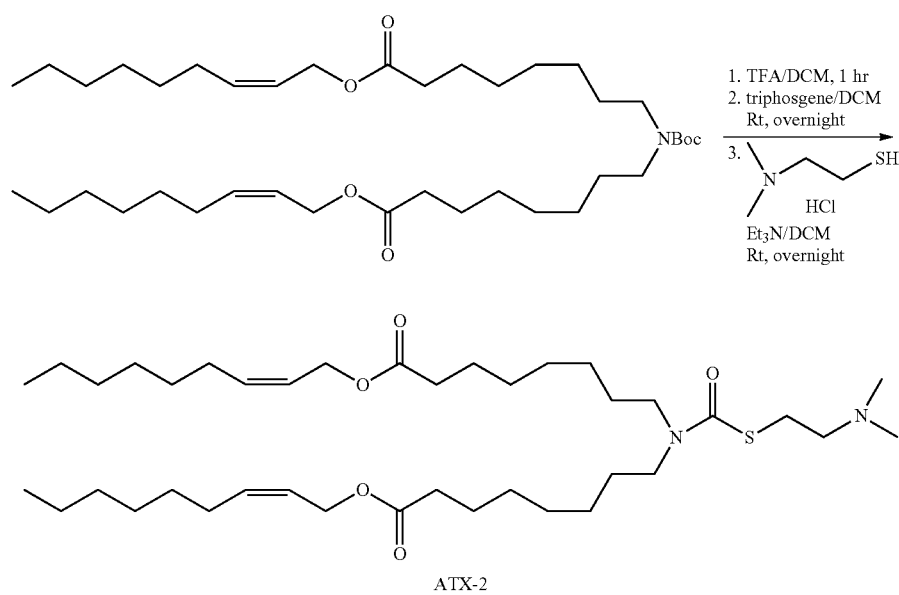

ATX-2

Example 10

Synthesis of ATX-003

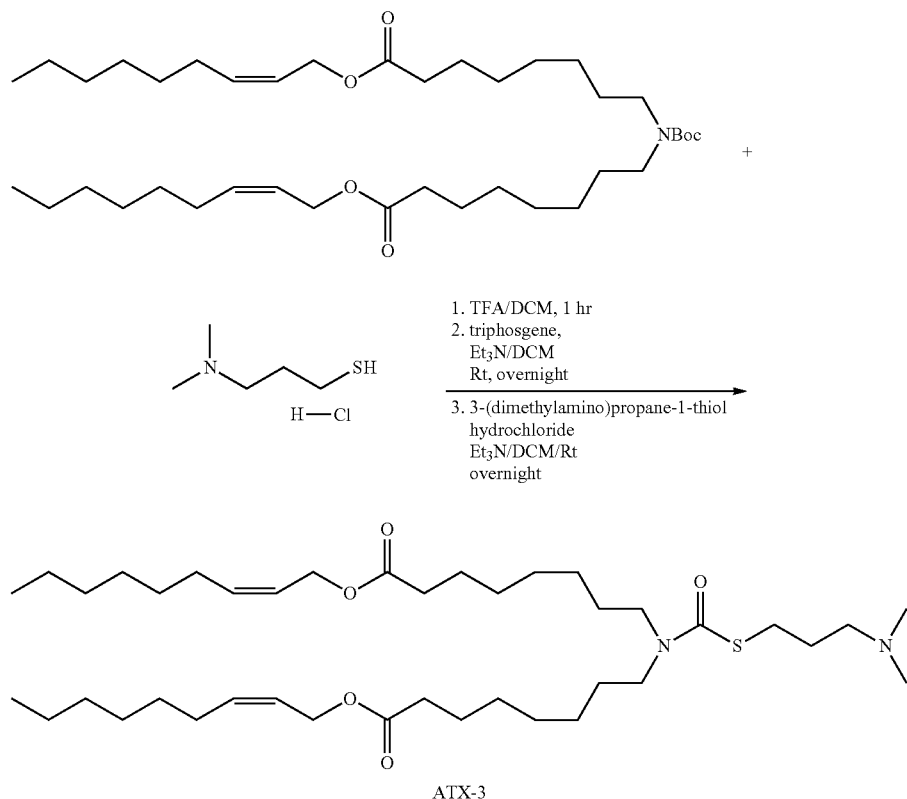

Di((Z)-non-2-en-1-yl) 8,8'((tertbutoxycarbonyl) azanediyl) dioctanoate (0.00337 mol, 2.2 g) was dissolved in dry DCM (20 ml). TFA was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO$_3$ solution. The aqueous layer was re-extracted with DCM, and the combined organic layers were washed with brine solution, dried over Na$_2$SO$_4$ and concentrated under reduced pressure. The collected crude product was dissolved in dry DCM (10 ml) under nitrogen gas. Triphosgene (0.0182 mol, 5.4 g) was added and the reaction mixture was cooled to 0° C., and Et$_3$N was added drop wise. The reaction mixture was stirred overnight at room temperature. Thin layer chromatography showed that the reaction was completed. DCM solvent was removed from the reaction mass by distillation under N$_2$. The reaction product was cooled to 0° C., diluted with DCM (15 ml), and 2-(dimethylamino)propanethiol.HCl (0.0182 mol, 2.82 g) was added, followed by Et$_3$N (dry). The reaction mixture was then stirred overnight at room temperature. Thin layer chromatography showed that the reaction was completed. The reaction product was diluted with 0.3 M HCl aqueous solution (20 ml), and the organic layer was separated. The aqueous layer was re-extracted with DCM, and the combined organic layers were washed with 10% K$_2$CO$_3$ aqueous solution (50 ml) and dried over anhydrous Na$_2$SO$_4$. Concentration of the solvent gave a crude mass of 5 gram. The crude compound was purified by silica gel column (100-200 mesh) using 3% MeOH/DCM. The yield was 0.9 gram.

Example 11

Synthesis of ATX-004

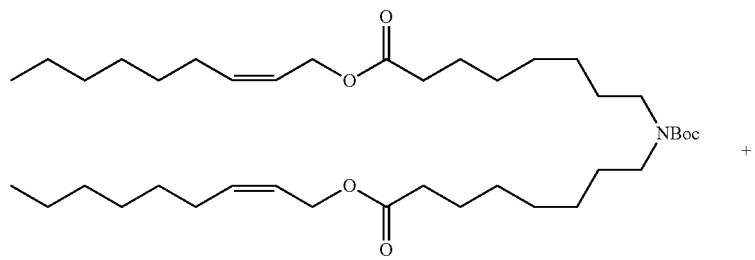

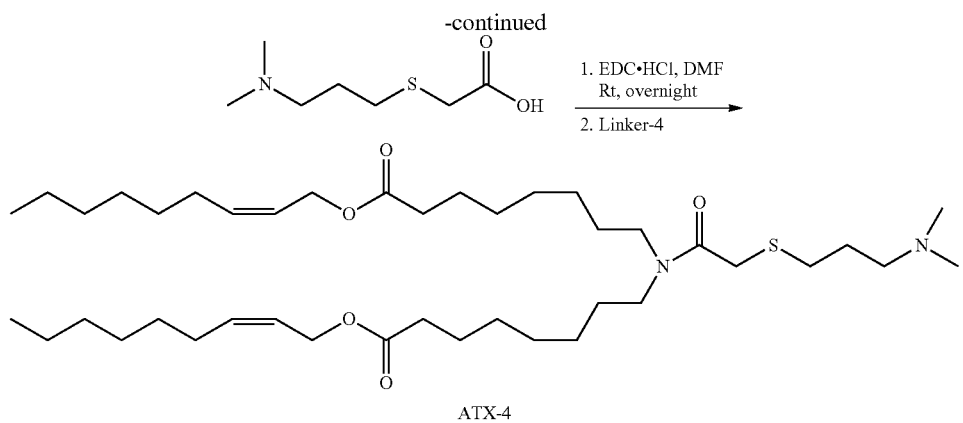

ATX-4

Di((Z)-non-2-en-1-yl) 8,8'((tertbutoxycarbonyl) azanediyl) dioctanoate (0.023 mol, 15 g) was dissolved in DCM (200 ml). TFA was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO$_3$ solution. The aqueous layer was re-extracted with DCM, and the combined organic layers were washed with brine solution, dried over Na$_2$SO$_4$ and concentrated. The collected crude product, di((Z)-non-2-en-1-yl)8,8'-azanediyldioctanoate (5.853 mmol, 3.2 g) was dissolved in dry dimethyl formamide (DMF) under nitrogen, and 2-((3-(dimethylamino)propyl)thio)acetic acid (10.48 mmol, 1.85 g) and EDC HCl (14.56 mmol, 2.78 g) was added. The reaction was stirred overnight at room temperature. The reaction was quenched with water (30 ml) and diluted with DCM (30 ml), and the organic layer was separated. The aqueous layer was re-extracted with DCM, and the combined organic layers were washed with 10% K$_2$CO$_3$ aqueous solution and dried over anhydrous Na$_2$SO$_4$. The crude compound was purified by silica gel column (100-200 mesh) using 3% MeOH/DCM. The yield was 1 gram (24.2%).

Example 12

Synthesis of ATX-005

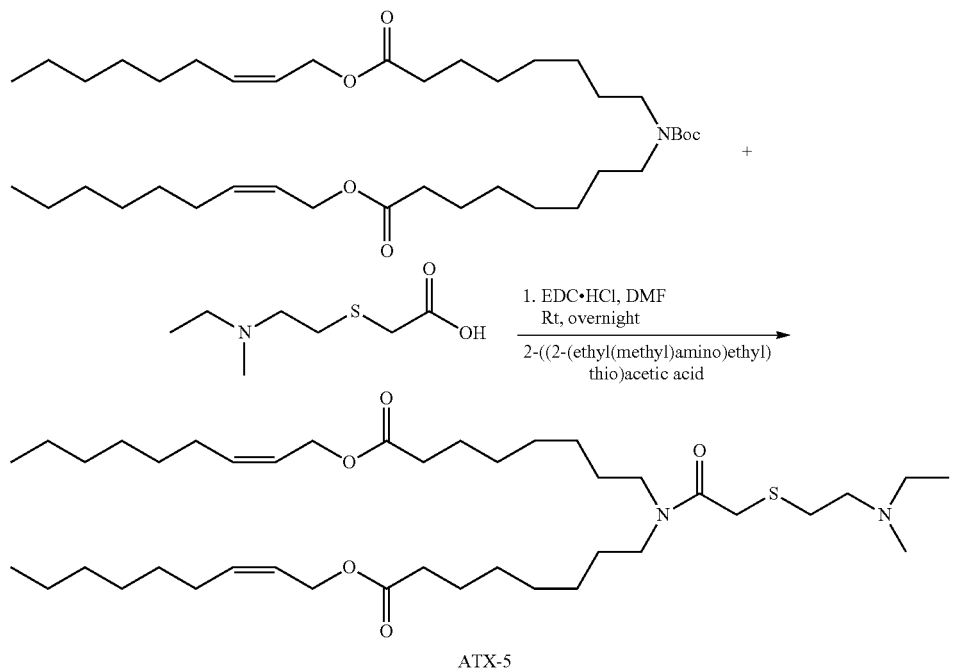

ATX-5

Di((Z)-non-2-en-1-yl) 8,8'((tertbutoxycarbonyl) azanediyl) dioctanoate (0.023 mol, 15 g) was dissolved in dry DCM (200 ml). TFA was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO$_3$ solution. The aqueous layer was re-extracted with DCM, and the combined organic layers were washed with brine solution, dried over Na$_2$SO$_4$ and concentrated. Crude reaction product, di((Z)-non-2-en-1-yl)8,8'-azanediyldioctanoate (5.853 mmol, 3.2 g) was dissolved in dimethylformamide (DMF) under nitrogen gas. 2-((3-(dimethylamino)propyl)thio)acetic acid (10.48 mmol, 1.85 g) and EDC-HCl (14.56 mmol, 2.78 g) were added and the reaction mixture was stirred overnight at room temperature. Thin layer chromatography showed that the reaction was completed. The reaction product was quenched with water (30 ml) and diluted with DCM (30 ml). The aqueous layer was re-extracted with DCM, and the combined organic layers were washed with 10% K$_2$CO$_3$ aqueous solution (75 ml) and dried over anhydrous Na$_2$SO$_4$. Concentration of the solvent gave a crude mass of 5 grams. Crude compound was purified by silica gel column (100-200 mesh) using 3% MeOH/DCM. The yield was 1 gram (24.2%).

Example 13

Synthesis of ATX-006 uct was concentrated under vacuum at 40° C. and the crude residue was diluted with DCM, and washed with a 10% NaHCO$_3$ solution. The aqueous layer was re-extracted with DCM, and the combined organic layers were washed with brine solution, dried over Na$_2$SO$_4$ and concentrated. The collected crude product was dissolved in dry DCM (85 ml) under nitrogen gas. Triphosgene were added and the reaction mixture was cooled to 0° C., and Et$_3$N was added drop wise. The reaction mixture was stirred overnight at room temperature. Thin layer chromatography showed that the reaction was completed. The crude reaction product was dissolved in dry DMF under nitrogen atmosphere, and 2-((2-(diethylamino)ethyl)thio)acetic acid (3.93 mmol, 751 mg) and EDC-HCl (5.45 mmol, 1.0 g) were added. The reaction mixture was stirred overnight at room temperature. The reaction was quenched with water (3 ml) and excess DMF was removed under vacuum at 25° C. The reaction product was diluted with water and aqueous layer was extracted thrice with DCM (20 ml). The combined organic layers were washed with brine solution and dried over anhydrous Na$_2$SO$_4$. Concentration of the solvent gave a crude mass of

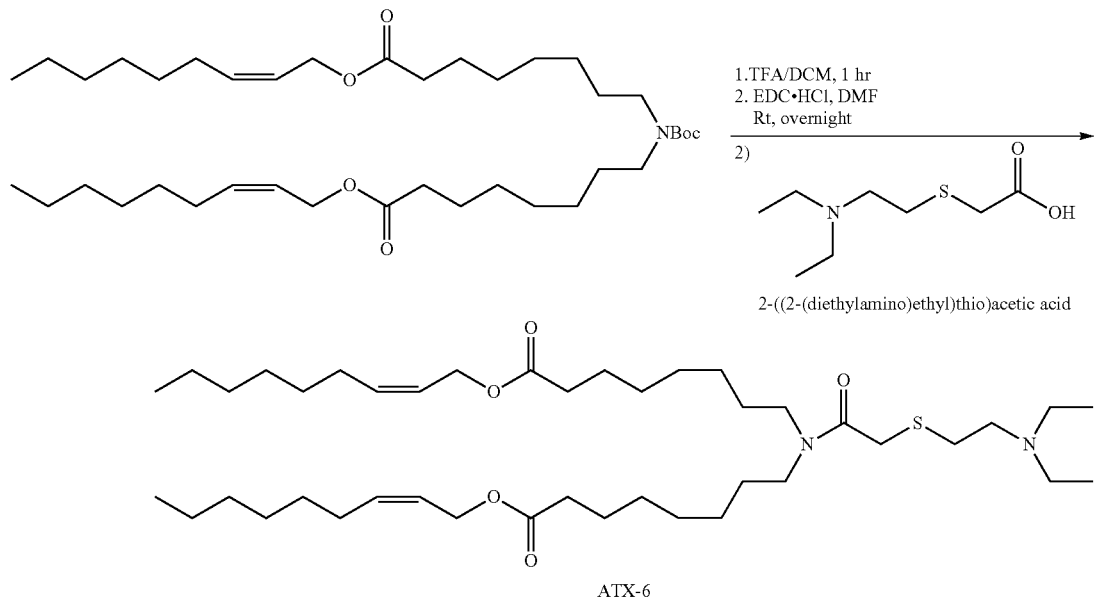

Di((Z)-non-2-en-1-yl) 8,8'((tertbutoxycarbonyl)azanediyl) dioctanoate was dissolved in dry DCM (150 ml). TFA was added at 0° C. to initiate a reaction. The reaction temperature was slowly allowed to warm to room temperature for 30 minutes with stirring. Thin layer chromatography showed that the reaction was completed. The reaction prod- 2 g. After purification by silica gel column (100-200 mesh) using 3% MeOH/DCM, the yield was 1.2 g (76%).

Example 14

Synthesis of ATX-009

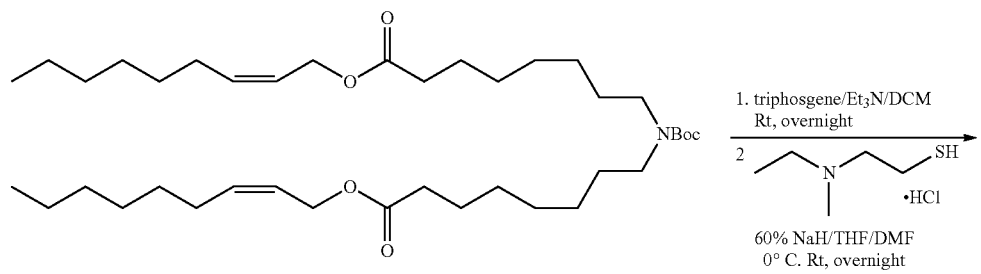

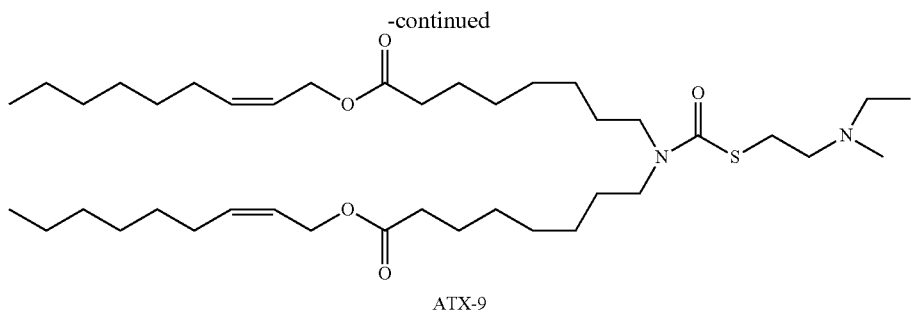

ATX-9

Di((Z)-non-2-en-1-yl) 8,8'((tertbutoxycarbonyl) azanediyl) dioctanoate (13.85 mmol, 9 grams) was dissolved in dry DCM (20 ml). TFA was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO₃ solution. The aqueous layer was re-extracted with DCM, and the combined organic layers were washed with brine solution, dried separated. The aqueous layer was re-extracted with ethyl acetate (EtOAc) (20 ml), washed in cold water and brine, and the combined organic layers were washed and dried over anhydrous Na₂SO₄. Concentration of the solvent gave 1 gram or crude product. The compound was purified by silica gel column (100-200 mesh) using 3% MeOH/DCM to yield 100 mg.

Example 15

Synthesis of ATX-010

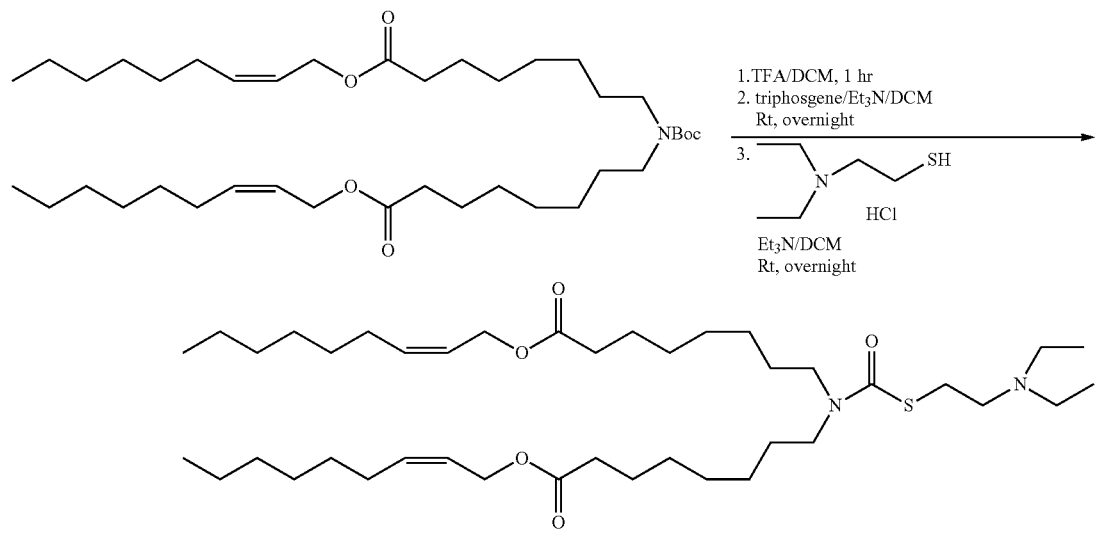

ATX-10 over Na₂SO₄ and concentrated. Di((Z)-non-2-en-1-yl)8,8'-azanediyldioctanoate (0.909 mmol, 500 mg) was dissolved in dry DCM (20 ml) under nitrogen atmosphere. Triphosgene were added and the reaction mixture was cooled to 0° C., and Et₃N was added drop wise. The reaction mixture was stirred overnight at room temperature. Thin layer chromatography showed that the reaction was completed. DCM solvent was removed from the reaction mass by distillation under nitrogen atmosphere. 2-(ethyl(methyl)amino)ethane-1-thiol hydrochloride (4.575 mmol, 715 mg) was dissolved in DMF (7 ml) and tetrahydrofuran (THF) (5 ml), and was added drop wise to the sodium hydride suspension in THF at 0° C. The reaction mixture was then stirred overnight at room temperature. Thin layer chromatography showed that the reaction was completed. The reaction product was diluted with ethyl acetate and cold water. The reaction was neutralized with 5% HCl (9 ml), and the organic layer was Di((Z)-non-2-en-1-yl) 8,8'((tertbutoxycarbonyl) azanediyl) dioctanoate (3.079 mmol, 2 g) was dissolved in dry DCM (20 ml). TFA was added at 0° C. to initiate a reaction. The reaction temperature was slowly allowed to warm to room temperature for 30 minutes with stirring. Thin layer chromatography showed that the reaction was completed. The reaction product was concentrated under vacuum at 40° C. and the crude residue was diluted with DCM, and washed with a 10% NaHCO₃ solution. The aqueous layer was re-extracted with DCM, and the combined organic layers were washed with brine solution, dried over Na₂SO₄ and concentrated. The collected crude product was dissolved in dry DCM (20 ml) under nitrogen gas. Triphosgene (14.55 mmol, 4.32 g) was added and the reaction mixture was cooled to 0° C., and Et₃N was added drop wise. The reaction mixture was stirred overnight at room temperature.

Thin layer chromatography showed that the reaction was completed. DCM solvent was removed from the reaction mass by distillation under $N_2$. The reaction product was cooled to 0° C., diluted with DCM (20 ml), and 2-(dimethylamino)ethanethiol HCl (0.063 mol, 8.3 g) was added, followed by $Et_3N$ (dry). The reaction mixture was then stirred overnight at room temperature.

Thin layer chromatography showed that the reaction was completed. The reaction product was diluted with 0.3 M HCl solution (20 ml), and the organic layer was separated. The aqueous layer was re-extracted with DCM, and the combined organic layers were washed with 10% $K_2CO_3$ aqueous solution 20 ml) and dried over anhydrous $Na_2SO_4$. Concentration of the solvent gave a crude mass of 10 gram. The crude compound was purified by silica gel column (100-200 mesh) using 3% MeOH/DCM. The yield was 1.4 g (75%).

Example 16

Synthesis of ATX-011 to ATX-017, ATX-021 to ATX-023, and ATX-026 to ATX-030 from Table 1, and the Compounds of Tables 2 and 3

The synthesis of ATX-011 to ATX-017, ATX-021 to ATX-023, and ATX-026 to ATX-030 and the compounds of Tables 2 and 3 follows the synthesis of Examples 1 to 15, by substituting appropriate starting ingredients for synthetic reactions described therein.

Example 17

In Vivo Mouse Factor VII Silencing

Using a liver-directed in vivo screen of the liposome libraries, a series of compounds were tested that facilitate high levels of siRNA mediated gene silencing in hepatocytes, the cells comprising the liver parenchyma. Factor VII, a blood clotting factor, is a suitable target gene for assaying functional siRNA delivery to liver. Because this factor is produced specifically in hepatocytes, gene silencing indicates successful delivery to parenchyma, as opposed to delivery to the cells of the reticulo-endothelial system (e.g., Kupffer cells). Furthermore, Factor VII is a secreted protein that can be readily measured in serum, obviating the need to euthanize animals. Silencing at the mRNA level can be readily determined by measuring levels of protein. This is because the protein's short half-life (2-5 hour). C57BL/6 mice (Charles River Labs) received either saline or siRNA in liposome formulations via tail vein injection at a volume of 0.006 ml/g. At 48 h after administration, animals were anesthetized by isofluorane inhalation and blood was collected into serum separator tubes by retroorbital bleed. Serum levels of Factor VII protein were determined in samples using a chromogenic assay (Biophen FVII, Aniara Corporation) according to manufacturers' protocols. A standard curve was generated using serum collected from saline-treated animals.

Figure 2:
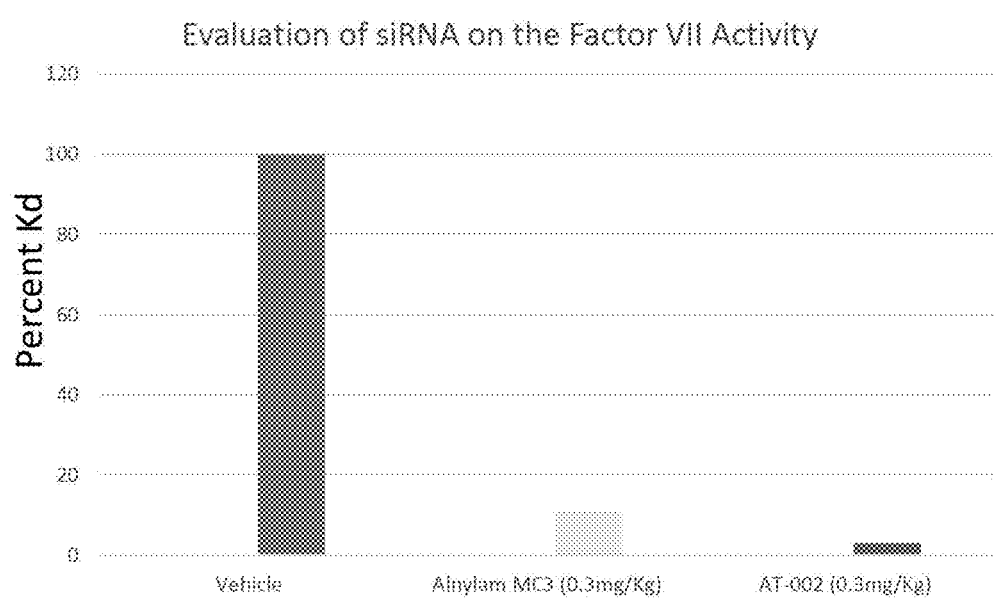
FIG. 2 shows an evaluation of the effect of siRNA of Factor VII activity based on the results shown in FIG. 2, and normalized to percentage knockdown compared to the vehicle alone.

Compositions with siRNA directed to Factor VIII were formulated with ATX-001, ATX-002, ATX-003, and ATX-547, and comparator samples NC1 and MC3 (Alnylam). These were injected into animals at 0.3 mg/kg and at 1 mg/kg. The siRNA encapsulated by MC3 (0.3 mg/kg), NC1 (0.3 mg/kg), ATX-547 (0.3 mg/kg), ATX-001 (0.3 and 1.0 mg/kg), ATX-002 (0.3 and 1.0 mg/kg), and ATX-003 (0.3 and 1.0 mg/kg) was measured for the ability to knockdown Factor VII in mouse plasma following administration of the siRNA formulation to C57BL6 mice. The results showed that ATX-001 and ATX-002 were most effective at 0.3 mg/kg, compared to controls (FIGS. 1 and 2).

Figure 3:
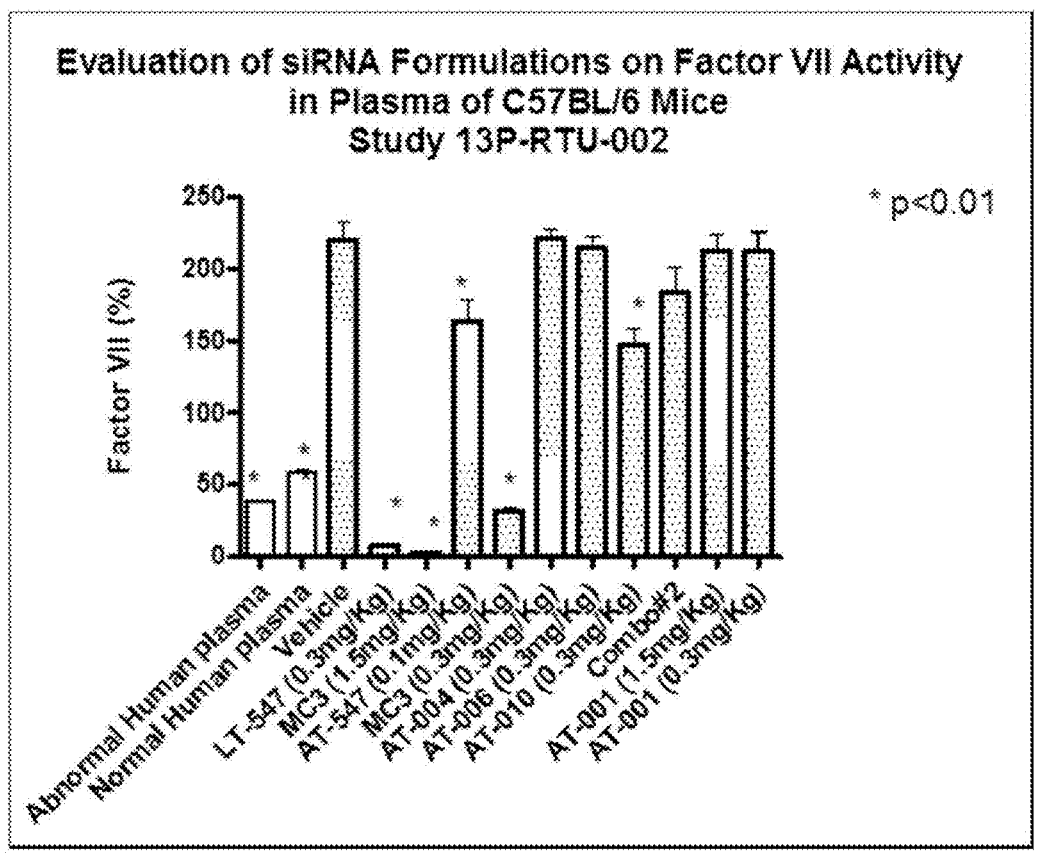
FIG. 3 shows the knockdown activity of siRNA encapsulated by different cationic lipids. The lipids include MC3 (0.3 and 1.5 mg/kg), NC1 (0.3 mg/kg), AT547 (0.1 and 0.3 mg/kg), AT004 (0.3), AT006 (0.3 and 1.0 mg/kg), ATX-010 (0.3 mg/kg), and AT001 (0.3 and 1.5 mg/kg). The amount of Factor VII knockdown in mouse plasma is shown following administration of the siRNA formulation to C57BL6 mice, compared to injection of vehicle alone. The amount of Factor VII in abnormal and normal human plasma is included as a control. Statistically significant decreases in Factor VII levels (p<0.01) is shown by an asterisk (*).
Figure 4:
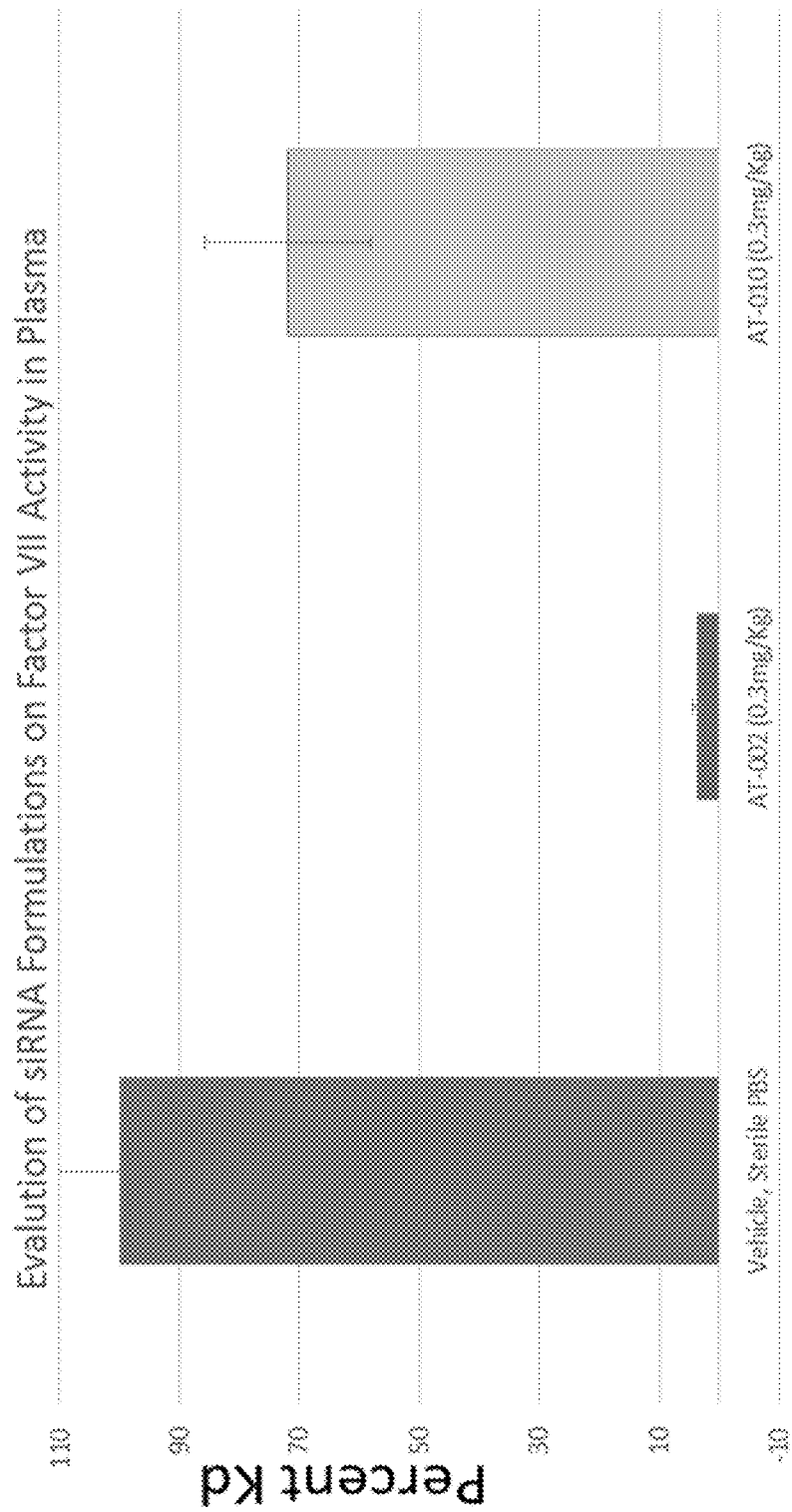
FIG. 4 shows an evaluation of the effect of siRNA of Factor VII activity based on the results shown in FIG. 2, and normalized to percentage knockdown compared to the vehicle alone.

The siRNA encapsulated MC3 (0.3 and 1.5 mg/kg), NC1 (0.3 mg/kg), ATX-547 (0.1 and 0.3 mg/kg), ATX-004 (0.3), ATX-006 (0.3 and 1.0 mg/kg), ATX-010 (0.3 mg/kg), and ATX-001 (0.3 and 1.5 mg/kg), was measured for Factor VII knockdown in mouse plasma following administration of the siRNA formulation to C57BL6 mice. The results showed that ATX-001 and ATX-010 were most effective (FIGS. 3 and 4). The knockdown activity of the exemplary compounds is shown for 0.3 mg/kg or at 0.05 mg/kg for ATX-018, ATX-019, and ATX-020 (Table 1).

What is claimed:
1. A compound of formula I

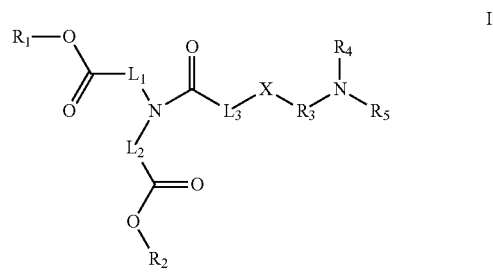

wherein
$R_1$ is a linear alkyl having 5 to 10 carbons,
$R_2$ is a branched alkyl having 12 to 20 carbons and consisting of one branch,
$L_1$ and $L_2$ are independently a bond or linear alkylene of 1-3 carbons,
X is S or O,
$L_3$ is a bond,
$R_3$ is an alkylene of 1 to 6 carbons, and
$R_4$ and $R_5$ are the same or different, each a linear or branched alkyl of 1 to 6 carbons;
or a pharmaceutically acceptable salt thereof.

2. The compound of claim 1, wherein $L_1$ and $L_2$ are the same.

3. The compound of claim 1, wherein $R_4$ and $R_5$ are the same or different, each a methyl, ethyl, n-propyl, isopropyl, n-butyl, t-butyl, n-pentyl, or hexyl.

4. The compound of claim 1, wherein $R_4$ and $R_5$ are the same or different, each a methyl, ethyl, n-propyl, or isopropyl.

5. The compound of claim 1, wherein X is S.

6. A compound of formula I

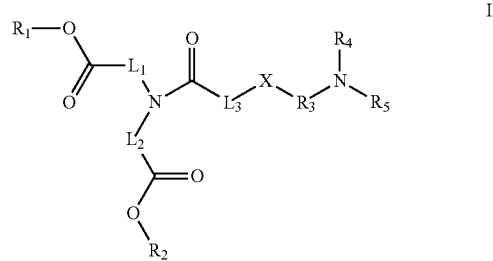

wherein
$R_1$ and $R_2$ are a branched alkyl having 12 to 20 carbons and consisting of one branch, $L_1$ and $L_2$ are independently a bond or a linear alkylene of 1-3 carbons,
X is S or O,
$L_3$ is a bond,
$R_3$ is an alkylene of 1 to 6 carbons, and
$R_4$ and $R_5$ are the same or different, each a linear or branched alkyl of 1 to 6 carbons;
or a pharmaceutically acceptable salt thereof.

7. The compound of claim 6, wherein $L_1$ and $L_2$ are the same.

8. The compound of claim 6, wherein $R_4$ and $R_5$ are the same or different, each a methyl, ethyl, n-propyl, isopropyl, n-butyl, t-butyl, n-pentyl, or hexyl.

9. The compound of claim 6, wherein $R_4$ and $R_5$ are the same or different, each a methyl, ethyl, n-propyl, or isopropyl.

10. The compound of claim 6, wherein X is S.

11. The compound of claim 6, wherein $L_1$ and $L_2$ are each a bond.

12. The compound of claim 1 selected from the group consisting of

ATX-B-7

ATX-B-8 and

ATX-B-9

13. The compound of claim 6 selected from the group consisting of

ATX-B-1

ATX-B-2

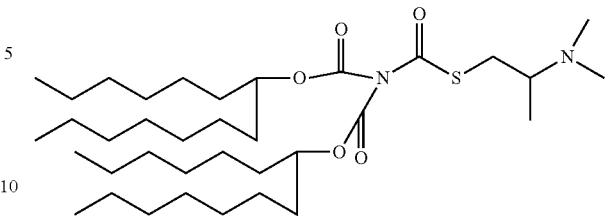

ATX-B-3

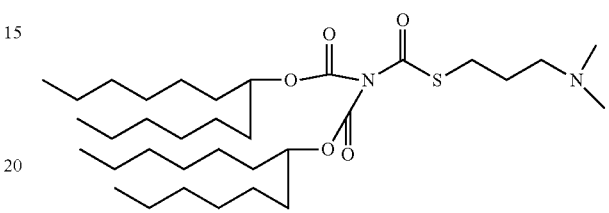

ATX-B-4

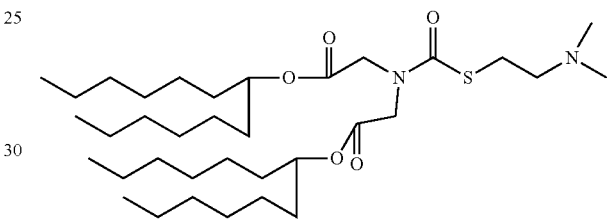

ATX-B-5

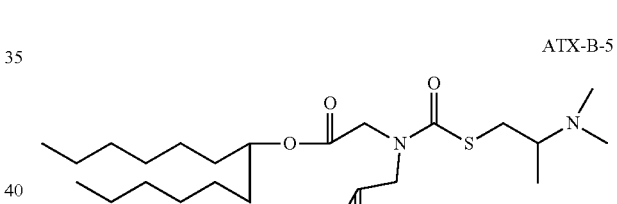

ATX-B-6

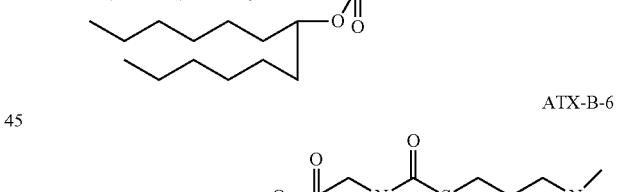

and

ATX-B-10

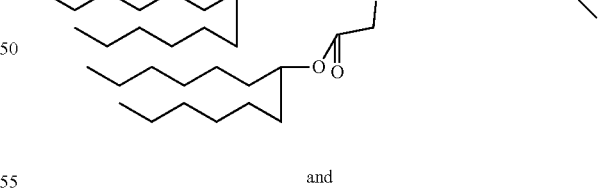

14. A compound having the structure
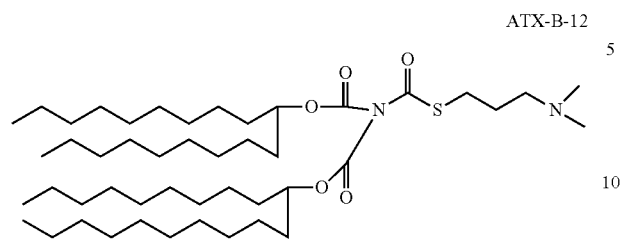
ATX-B-12
or a pharmaceutically acceptable salt thereof.
* * * * *